US009044457B2

(12) United States Patent
Dimitrov et al.

(10) Patent No.: US 9,044,457 B2
(45) Date of Patent: Jun. 2, 2015

(54) ANTI-DR4 AGONIST ANTIBODIES

(75) Inventors: Dimiter Dimitrov, Frederick, MD (US); Yang Feng, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 191 days.

(21) Appl. No.: 13/704,577

(22) PCT Filed: Jun. 16, 2011

(86) PCT No.: PCT/US2011/040750
§ 371 (c)(1),
(2), (4) Date: Feb. 26, 2013

(87) PCT Pub. No.: WO2011/159928
PCT Pub. Date: Dec. 22, 2011

(65) Prior Publication Data
US 2013/0156781 A1  Jun. 20, 2013

Related U.S. Application Data

(60) Provisional application No. 61/355,349, filed on Jun. 16, 2010.

(51) Int. Cl.
A61K 39/395 (2006.01)
C07K 16/30 (2006.01)
C12N 5/10 (2006.01)
C12N 15/13 (2006.01)
C07K 16/28 (2006.01)
A61K 45/06 (2006.01)

(52) U.S. Cl.
CPC ......... *A61K 39/3955* (2013.01); *C07K 16/2878* (2013.01); *C07K 2317/55* (2013.01); *C07K 2317/76* (2013.01); *A61K 45/06* (2013.01); *C07K 2317/34* (2013.01)

(58) Field of Classification Search
None
See application file for complete search history.

(56) References Cited

U.S. PATENT DOCUMENTS

| 7,252,994 | B2 | 8/2007 | Chuntharapai et al. |
| 7,476,383 | B2 * | 1/2009 | Zhou et al. |
| 2003/0073187 | A1 | 4/2003 | Ni et al. |
| 2004/0120947 | A1 | 6/2004 | Ashkenazi et al. |
| 2004/0147725 | A1 | 7/2004 | Chuntharapai et al. |
| 2009/0226429 | A1 * | 9/2009 | Salcedo et al. |

OTHER PUBLICATIONS

Chen et al., Enhancement and destruction of antibody function by somatic mutation: unequal occurrence is controlled by V gene combinatorial associations, The EMBO J., 14(12):2784-2794, 1995.*
Rudikoff et al., Single amino acid substitution altering antigen-binding specificty, Proc. Natl. Acad. Sci, USA, 79:1979-1983, 1982.*

(Continued)

*Primary Examiner* — Claire Kaufman
(74) *Attorney, Agent, or Firm* — Kilpatrick Townsend & Stockton LLP

(57) ABSTRACT

The present invention provides antibodies and antibody fragments that specifically recognize and agonize the death receptor 4 (DR4). Also provided in the invention are polynucleotides and vectors that encode such molecules and host cells that harbor the polynucleotides or vectors.

21 Claims, 7 Drawing Sheets

(56) References Cited

OTHER PUBLICATIONS

International Search Report and Written Opinion dated Jun. 27, 2012, received in related International Application No. PCT/US2011/040750, filed Jun. 16, 2011.

Voelkel-Johnson et al., "An Antibody Against DR4 (Trail-R1) in Combination with Doxorubicin Selectively Kills Malignant by Not Normal Prostate Cells," 2003, Cancer Biology & Therapy, 2:3, pp. 283-288.

* cited by examiner

SEQUENCE LISTING

<160> NUMBER OF SEQ ID NOS: 40

<210> SEQ ID NO 1
<211> LENGTH: 216
<212> TYPE: PRT
<213> ORGANISM: Artificial Sequence
<220> FEATURE:
<223> OTHER INFORMATION: synthetic anti-DR4 monoclonal antibody M921
      light chain variable region

<400> SEQUENCE: 1

Gln Pro Val Leu Thr Gln Pro Pro Ser Ala Ser Ala Thr Pro Gly Gln
 1               5                   10                  15

Arg Val Thr Ile Ser Cys Ser Gly Ser Ser Ser Asn Ile Gly Ser Asn
                20                  25                  30

Thr Leu Asp Trp Phe Gln Gln Leu Pro Gly Thr Ala Pro Lys Leu Leu
            35                  40                  45

```
Ile Phe Asp Thr Asn Arg Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ala Glu Asp Glu Ala Val Tyr Phe Cys Ala Thr Trp Asp Asn Ser Leu
                 85                  90                  95

Asn Gly Ala Val Phe Gly Gly Gly Thr Lys Leu Ser Val Pro Arg Gln
                100                 105                 110

Ala Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 2
<211> LENGTH: 240
<212> TYPE: PRT
<213> ORGANISM: Artificial Sequence
<220> FEATURE:
<223> OTHER INFORMATION: synthetic anti-DR4 monoclonal antibody M921 heavy chain variable region

<400> SEQUENCE: 2

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Gly Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Asp Leu Gly Val Ala Ala Asp Ser Tyr Tyr
                100                 105                 110

Tyr Tyr Gly Met Asp Val Trp Gly Gln Gly Thr Thr Val Thr Val Ser
            115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
```

```
                  180                 185                 190
Ser Leu Ser Ser Val Val Thr Val Pro Ser Ser Leu Gly Thr Gln
            195                 200                 205

Thr Tyr Ile Cys Asn Val Asn His Lys Pro Ser Asn Thr Lys Val Asp
        210                 215                 220

Lys Lys Val Gly Pro Lys Ser Cys Asp Lys Thr Ser Gly Gln Ala Gly
225                 230                 235                 240

<210> SEQ ID NO 3
<211> LENGTH: 217
<212> TYPE: PRT
<213> ORGANISM: Artificial Sequence
<220> FEATURE:
<223> OTHER INFORMATION: synthetic anti-DR4 monoclonal antibody M922
      light chain variable region

<400> SEQUENCE: 3

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Ser Leu
            85                  90                  95

Asn Gly Arg Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
        180                 185                 190

His Lys Ser Tyr Ser Cys Gln Val Thr His Glu Gly Ser Thr Val Glu
            195                 200                 205

Lys Thr Val Ala Pro Thr Glu Cys Ser
        210                 215

<210> SEQ ID NO 4
<211> LENGTH: 233
<212> TYPE: PRT
<213> ORGANISM: Artificial Sequence
<220> FEATURE:
<223> OTHER INFORMATION: synthetic anti-DR4 monoclonal antibody M922
      heavy chain variable region

<400> SEQUENCE: 4

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
```

```
                    20                  25                  30
Ser Ala Ala Trp Asn Trp Ile Arg Gln Ser Pro Ser Arg Gly Leu Glu
            35                  40                  45
Trp Leu Gly Arg Thr Tyr Tyr Arg Ser Lys Trp Tyr Asn Asp Tyr Ala
        50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg Glu Thr Val Ala Val Asp Ala Phe Asp Ile Trp
            100                 105                 110
Gly Gln Gly Thr Met Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Ser Val Asn
        195                 200                 205
His Lys Pro Ser Asn Thr Lys Val Asp Lys Lys Val Glu Pro Lys Ser
    210                 215                 220
Cys Asp Lys Thr Ser Gly Gln Ala Gly
225                 230

<210> SEQ ID NO 5
<211> LENGTH: 8
<212> TYPE: PRT
<213> ORGANISM: Artificial Sequence
<220> FEATURE:
<223> OTHER INFORMATION: synthetic anti-DR4 monoclonal antibody M921 and
      M922 light chain CDR1

<400> SEQUENCE: 5

Ser Ser Asn Ile Gly Ser Asn Thr
1               5

<210> SEQ ID NO 6
<211> LENGTH: 3
<212> TYPE: PRT
<213> ORGANISM: Artificial Sequence
<220> FEATURE:
<223> OTHER INFORMATION: synthetic anti-DR4 monoclonal antibody M921
      light chain CDR2

<400> SEQUENCE: 6

Asp Thr Asn
1

<210> SEQ ID NO 7
<211> LENGTH: 12
<212> TYPE: PRT
<213> ORGANISM: Artificial Sequence
<220> FEATURE:
<223> OTHER INFORMATION: synthetic anti-DR4 monoclonal antibody M921
      light chain CDR3

<400> SEQUENCE: 7
```

Ala Thr Trp Asp Asn Ser Leu Asn Gly Ala Val Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: synthetic anti-DR4 monoclonal antibody M921 and
      M922 heavy chain CDR1

<400> SEQUENCE: 8

Gly Asp Ser Val Ser Ser Asn Ser Ala Ala
1               5                   10

<210> SEQ ID NO 9
<211> LENGTH: 9
<212> TYPE: PRT
<213> ORGANISM: Artificial Sequence
<220> FEATURE:
<223> OTHER INFORMATION: synthetic anti-DR4 monoclonal antibody M921 and
      M922 heavy chain CDR2

<400> SEQUENCE: 9

Thr Tyr Tyr Arg Ser Lys Trp Tyr Asn
1               5

<210> SEQ ID NO 10
<211> LENGTH: 20
<212> TYPE: PRT
<213> ORGANISM: Artificial Sequence
<220> FEATURE:
<223> OTHER INFORMATION: synthetic anti-DR4 monoclonal antibody M921
      heavy chain CDR3

<400> SEQUENCE: 10

Ala Arg Asp Leu Gly Val Ala Ala Ala Asp Ser Tyr Tyr Tyr Gly
1               5                   10                  15

Met Asp Val Trp
            20

<210> SEQ ID NO 11
<211> LENGTH: 3
<212> TYPE: PRT
<213> ORGANISM: Artificial Sequence
<220> FEATURE:
<223> OTHER INFORMATION: synthetic anti-DR4 monoclonal antibody M922
      light chain CDR2

<400> SEQUENCE: 11

Ser Asn Asn
1

<210> SEQ ID NO 12
<211> LENGTH: 13
<212> TYPE: PRT
<213> ORGANISM: Artificial Sequence
<220> FEATURE:
<223> OTHER INFORMATION: synthetic anti-DR4 monoclonal antibody M922
      light chain CDR3

<400> SEQUENCE: 12

Ala Ala Trp Asp Asp Ser Leu Asn Gly Arg Val Val Phe
1               5                   10

<210> SEQ ID NO 13

```
<211> LENGTH: 13
<212> TYPE: PRT
<213> ORGANISM: Artificial Sequence
<220> FEATURE:
<223> OTHER INFORMATION: synthetic anti-DR4 monoclonal antibody M922
      heavy chain CDR3

<400> SEQUENCE: 13

Ala Arg Glu Thr Val Ala Val Asp Ala Phe Asp Ile Trp
1               5                   10

<210> SEQ ID NO 14
<211> LENGTH: 25
<212> TYPE: PRT
<213> ORGANISM: Artificial Sequence
<220> FEATURE:
<223> OTHER INFORMATION: synthetic anti-DR4 monoclonal antibody M921
      light chain FR1

<400> SEQUENCE: 14

Gln Pro Val Leu Thr Gln Pro Pro Ser Ala Ser Ala Thr Pro Gly Gln
1               5                   10                  15

Arg Val Thr Ile Ser Cys Ser Gly Ser
            20                  25

<210> SEQ ID NO 15
<211> LENGTH: 17
<212> TYPE: PRT
<213> ORGANISM: Artificial Sequence
<220> FEATURE:
<223> OTHER INFORMATION: synthetic anti-DR4 monoclonal antibody M921
      light chain FR2

<400> SEQUENCE: 15

Leu Asp Trp Phe Gln Gln Leu Pro Gly Thr Ala Pro Lys Leu Leu Ile
1               5                   10                  15

Phe

<210> SEQ ID NO 16
<211> LENGTH: 36
<212> TYPE: PRT
<213> ORGANISM: Artificial Sequence
<220> FEATURE:
<223> OTHER INFORMATION: synthetic anti-DR4 monoclonal antibody M921
      light chain FR3

<400> SEQUENCE: 16

Arg Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ala Glu Asp Glu Ala
            20                  25                  30

Val Tyr Phe Cys
        35

<210> SEQ ID NO 17
<211> LENGTH: 10
<212> TYPE: PRT
<213> ORGANISM: Artificial Sequence
<220> FEATURE:
<223> OTHER INFORMATION: synthetic anti-DR4 monoclonal antibody M921
      light chain FR4

<400> SEQUENCE: 17

Gly Gly Gly Thr Lys Leu Ser Val Pro Arg
1               5                   10
```

-continued

```
<210> SEQ ID NO 18
<211> LENGTH: 25
<212> TYPE: PRT
<213> ORGANISM: Artificial Sequence
<220> FEATURE:
<223> OTHER INFORMATION: synthetic anti-DR4 monoclonal antibody M921 and
      M922 heavy chain FR1

<400> SEQUENCE: 18

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 19
<211> LENGTH: 17
<212> TYPE: PRT
<213> ORGANISM: Artificial Sequence
<220> FEATURE:
<223> OTHER INFORMATION: synthetic anti-DR4 monoclonal antibody M921 and
      M922 heavy chain FR2

<400> SEQUENCE: 19

Trp Asn Trp Ile Arg Gln Ser Pro Ser Arg Gly Leu Glu Trp Leu Gly
1               5                   10                  15

Arg

<210> SEQ ID NO 20
<211> LENGTH: 38
<212> TYPE: PRT
<213> ORGANISM: Artificial Sequence
<220> FEATURE:
<223> OTHER INFORMATION: synthetic anti-DR4 monoclonal antibody M921
      heavy chain FR3

<400> SEQUENCE: 20

Asp Tyr Ala Val Ser Val Lys Gly Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 21
<211> LENGTH: 11
<212> TYPE: PRT
<213> ORGANISM: Artificial Sequence
<220> FEATURE:
<223> OTHER INFORMATION: synthetic anti-DR4 monoclonal antibody M921
      heavy chain FR4

<400> SEQUENCE: 21

Gly Gln Gly Thr Thr Val Thr Val Ser Ser Ala
1               5                   10

<210> SEQ ID NO 22
<211> LENGTH: 25
<212> TYPE: PRT
<213> ORGANISM: Artificial Sequence
<220> FEATURE:
<223> OTHER INFORMATION: synthetic anti-DR4 monoclonal antibody M922
      light chain FR1

<400> SEQUENCE: 22

Gln Ser Val Leu Thr Gln Pro Pro Ser Ala Ser Gly Thr Pro Gly Gln
```

```
                1               5                  10                  15
Arg Val Thr Ile Ser Cys Ser Gly Ser
                20                  25

<210> SEQ ID NO 23
<211> LENGTH: 17
<212> TYPE: PRT
<213> ORGANISM: Artificial Sequence
<220> FEATURE:
<223> OTHER INFORMATION: synthetic anti-DR4 monoclonal antibody M922
      light chain FR2

<400> SEQUENCE: 23

Val Asn Trp Tyr Gln Gln Leu Pro Gly Thr Ala Pro Lys Leu Leu Ile
 1               5                  10                  15
Tyr

<210> SEQ ID NO 24
<211> LENGTH: 36
<212> TYPE: PRT
<213> ORGANISM: Artificial Sequence
<220> FEATURE:
<223> OTHER INFORMATION: synthetic anti-DR4 monoclonal antibody M922
      light chain FR3

<400> SEQUENCE: 24

Gln Arg Pro Ser Gly Val Pro Asp Arg Phe Ser Gly Ser Lys Ser Gly
 1               5                  10                  15

Thr Ser Ala Ser Leu Ala Ile Ser Gly Leu Gln Ser Glu Asp Glu Ala
                20                  25                  30

Asp Tyr Tyr Cys
                35

<210> SEQ ID NO 25
<211> LENGTH: 11
<212> TYPE: PRT
<213> ORGANISM: Artificial Sequence
<220> FEATURE:
<223> OTHER INFORMATION: synthetic anti-DR4 monoclonal antibody M922
      light chain FR4

<400> SEQUENCE: 25

Phe Gly Gly Gly Thr Lys Leu Thr Val Leu Gly
 1               5                  10

<210> SEQ ID NO 26
<211> LENGTH: 38
<212> TYPE: PRT
<213> ORGANISM: Artificial Sequence
<220> FEATURE:
<223> OTHER INFORMATION: synthetic anti-DR4 monoclonal antibody M922
      heavy chain FR3

<400> SEQUENCE: 26

Asp Tyr Ala Val Ser Val Lys Ser Arg Ile Thr Ile Asn Pro Asp Thr
 1               5                  10                  15

Ser Lys Asn Gln Phe Ser Leu Gln Leu Asn Ser Val Thr Pro Glu Asp
                20                  25                  30

Thr Ala Val Tyr Tyr Cys
                35

<210> SEQ ID NO 27
<211> LENGTH: 11
<212> TYPE: PRT
```

-continued

<213> ORGANISM: Artificial Sequence
<220> FEATURE:
<223> OTHER INFORMATION: synthetic anti-DR4 monoclonal antibody M922
      heavy chain FR4

<400> SEQUENCE: 27

Gly Gln Gly Thr Met Val Thr Val Ser Ser Ala
1               5                   10

<210> SEQ ID NO 28
<211> LENGTH: 17
<212> TYPE: PRT
<213> ORGANISM: Artificial Sequence
<220> FEATURE:
<223> OTHER INFORMATION: synthetic anti-DR4 monoclonal antibody light
      chain FR2 consensus sequence
<220> FEATURE:
<221> NAME/KEY: VARIANT
<222> LOCATION: (1)...(1)
<223> OTHER INFORMATION: Xaa = Leu or Val
<220> FEATURE:
<221> NAME/KEY: VARIANT
<222> LOCATION: (17)...(17)
<223> OTHER INFORMATION: Xaa = Phe or Tyr

<400> SEQUENCE: 28

Xaa Asx Trp Phe Gln Gln Leu Pro Gly Thr Ala Pro Lys Leu Leu Ile
1               5                   10                  15

Xaa

<210> SEQ ID NO 29
<211> LENGTH: 36
<212> TYPE: PRT
<213> ORGANISM: Artificial Sequence
<220> FEATURE:
<223> OTHER INFORMATION: synthetic anti-DR4 monoclonal antibody light
      chain FR3 consensus sequence
<220> FEATURE:
<221> NAME/KEY: VARIANT
<222> LOCATION: (1)...(1)
<223> OTHER INFORMATION: Xaa = Arg or Gln
<220> FEATURE:
<221> NAME/KEY: VARIANT
<222> LOCATION: (28)...(28)
<223> OTHER INFORMATION: Xaa = Ala or Ser
<220> FEATURE:
<221> NAME/KEY: VARIANT
<222> LOCATION: (33)...(33)
<223> OTHER INFORMATION: Xaa = Val or Asp
<220> FEATURE:
<221> NAME/KEY: VARIANT
<222> LOCATION: (35)...(35)
<223> OTHER INFORMATION: Xaa = Phe or Tyr

<400> SEQUENCE: 29

Xaa Arg Pro Ser Gly Val Pro Asp Arg Phe Ser Gly Ser Lys Ser Gly
1               5                   10                  15

Thr Ser Ala Ser Leu Ala Ile Ser Gly Leu Gln Xaa Glu Asp Glu Ala
            20                  25                  30

Xaa Tyr Xaa Cys
        35

<210> SEQ ID NO 30
<211> LENGTH: 38
<212> TYPE: PRT
<213> ORGANISM: Artificial Sequence
<220> FEATURE:
<223> OTHER INFORMATION: synthetic anti-DR4 monoclonal antibody heavy
      chain FR3 consensus sequence
<220> FEATURE:

```
<221> NAME/KEY: VARIANT
<222> LOCATION: (8)...(8)
<223> OTHER INFORMATION: Xaa = Ser or Gly

<400> SEQUENCE: 30

Asp Tyr Ala Val Ser Val Lys Xaa Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 31
<211> LENGTH: 3
<212> TYPE: PRT
<213> ORGANISM: Artificial Sequence
<220> FEATURE:
<223> OTHER INFORMATION: synthetic anti-DR4 monoclonal antibody light
      chain CDR2 consensus sequence
<220> FEATURE:
<221> NAME/KEY: VARIANT
<222> LOCATION: (1)...(1)
<223> OTHER INFORMATION: Xaa = Asp or Ser
<220> FEATURE:
<221> NAME/KEY: VARIANT
<222> LOCATION: (2)...(2)
<223> OTHER INFORMATION: Xaa = Asn or Thr

<400> SEQUENCE: 31

Xaa Xaa Asn
1

<210> SEQ ID NO 32
<211> LENGTH: 13
<212> TYPE: PRT
<213> ORGANISM: Artificial Sequence
<220> FEATURE:
<223> OTHER INFORMATION: synthetic anti-DR4 monoclonal antibody light
      chain CDR3 consensus sequence
<220> FEATURE:
<221> NAME/KEY: VARIANT
<222> LOCATION: (2)...(2)
<223> OTHER INFORMATION: Xaa = Ala or Thr
<220> FEATURE:
<221> NAME/KEY: VARIANT
<222> LOCATION: (10)...(10)
<223> OTHER INFORMATION: Xaa = Ala or Arg
<220> FEATURE:
<221> NAME/KEY: VARIANT
<222> LOCATION: (12)...(12)
<223> OTHER INFORMATION: Xaa = Val or absent

<400> SEQUENCE: 32

Ala Xaa Trp Asp Asx Ser Leu Asn Gly Xaa Val Xaa Phe
1               5                   10

<210> SEQ ID NO 33
<211> LENGTH: 89
<212> TYPE: PRT
<213> ORGANISM: Artificial Sequence
<220> FEATURE:
<223> OTHER INFORMATION: synthetic anti-DR4 monoclonal antibody light
      chain variable segment (FR1-CDR1-FR2-CDR2-FR3) consensus
      sequence
<220> FEATURE:
<221> NAME/KEY: VARIANT
<222> LOCATION: (2)...(2)
<223> OTHER INFORMATION: Xaa = Pro or Ser
<220> FEATURE:
<221> NAME/KEY: VARIANT
<222> LOCATION: (12)...(12)
```

```
<223> OTHER INFORMATION: Xaa = Ala or Gly
<220> FEATURE:
<221> NAME/KEY: VARIANT
<222> LOCATION: (34)...(34)
<223> OTHER INFORMATION: Xaa = Leu or Val
<220> FEATURE:
<221> NAME/KEY: VARIANT
<222> LOCATION: (50)...(50)
<223> OTHER INFORMATION: Xaa = Phe or Tyr
<220> FEATURE:
<221> NAME/KEY: VARIANT
<222> LOCATION: (51)...(51)
<223> OTHER INFORMATION: Xaa = Asp or Ser
<220> FEATURE:
<221> NAME/KEY: VARIANT
<222> LOCATION: (52)...(52)
<223> OTHER INFORMATION: Xaa = Ser or Thr
<220> FEATURE:
<221> NAME/KEY: VARIANT
<222> LOCATION: (54)...(54)
<223> OTHER INFORMATION: Xaa = Arg or Gln
<220> FEATURE:
<221> NAME/KEY: VARIANT
<222> LOCATION: (81)...(81)
<223> OTHER INFORMATION: Xaa = Ala or Ser
<220> FEATURE:
<221> NAME/KEY: VARIANT
<222> LOCATION: (86)...(86)
<223> OTHER INFORMATION: Xaa = Asp or Val
<220> FEATURE:
<221> NAME/KEY: VARIANT
<222> LOCATION: (88)...(88)
<223> OTHER INFORMATION: Xaa = Phe or Tyr

<400> SEQUENCE: 33

Gln Xaa Val Leu Thr Gln Pro Pro Ser Ala Ser Xaa Thr Pro Gly Gln
 1               5                  10                  15

Arg Val Thr Ile Ser Cys Ser Gly Ser Ser Ser Asn Ile Gly Ser Asn
                20                  25                  30

Thr Xaa Asp Trp Phe Gln Gln Leu Pro Gly Thr Ala Pro Lys Leu Leu
            35                  40                  45

Ile Xaa Xaa Xaa Asn Xaa Arg Pro Ser Gly Val Pro Asp Arg Phe Ser
 50                  55                  60

Gly Ser Lys Ser Gly Thr Ser Ala Ser Leu Ala Ile Ser Gly Leu Gln
65                  70                  75                  80

Xaa Glu Asp Glu Ala Xaa Tyr Xaa Cys
                85

<210> SEQ ID NO 34
<211> LENGTH: 99
<212> TYPE: PRT
<213> ORGANISM: Artificial Sequence
<220> FEATURE:
<223> OTHER INFORMATION: synthetic anti-DR4 monoclonal antibody heavy
      chain variable segment (FR1-CDR1-FR2-CDR2-FR3) consensus
      sequence
<220> FEATURE:
<221> NAME/KEY: VARIANT
<222> LOCATION: (69)...(69)
<223> OTHER INFORMATION: Xaa = Ser or Gly

<400> SEQUENCE: 34

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45
```

-continued

```
Trp Leu Gly Arg Thr Tyr Tyr Arg Ser Lys Trp Tyr Asn Asp Tyr Ala
 50                  55                  60

Val Ser Val Lys Xaa Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys

<210> SEQ ID NO 35
<211> LENGTH: 468
<212> TYPE: PRT
<213> ORGANISM: Homo sapiens
<220> FEATURE:
<223> OTHER INFORMATION: human death receptor 4 (DR4), tumor necrosis
      factor-related apoptosis-inducing ligand receptor 1 (TRAIL-R1,
      TRAIL receptor 1), cytotoxic TRAIL receptor, tumor necrosis factor
      receptor superfamily member 10A (TNFRSF10A) precursor, APO2, CD261

<400> SEQUENCE: 35

Met Ala Pro Pro Ala Arg Val His Leu Gly Ala Phe Leu Ala Val
  1               5                  10                  15

Thr Pro Asn Pro Gly Ser Ala Ala Ser Gly Thr Glu Ala Ala Ala
                 20                  25                  30

Thr Pro Ser Lys Val Trp Gly Ser Ser Ala Gly Arg Ile Glu Pro Arg
                 35                  40                  45

Gly Gly Gly Arg Gly Ala Leu Pro Thr Ser Met Gly Gln His Gly Pro
 50                  55                  60

Ser Ala Arg Ala Arg Ala Gly Arg Ala Pro Gly Pro Arg Pro Ala Arg
 65                  70                  75                  80

Glu Ala Ser Pro Arg Leu Arg Val His Lys Thr Phe Lys Phe Val Val
                 85                  90                  95

Val Gly Val Leu Leu Gln Val Val Pro Ser Ser Ala Ala Thr Ile Lys
                100                 105                 110

Leu His Asp Gln Ser Ile Gly Thr Gln Gln Trp Glu His Ser Pro Leu
                115                 120                 125

Gly Glu Leu Cys Pro Pro Gly Ser His Arg Ser Glu His Pro Gly Ala
130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
                180                 185                 190

Gly Thr Phe Arg Asn Asp Asn Ser Ala Glu Met Cys Arg Lys Cys Ser
                195                 200                 205

Arg Gly Cys Pro Arg Gly Met Val Lys Val Lys Asp Cys Thr Pro Trp
210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
                245                 250                 255

Val Leu Ile Val Cys Cys Cys Ile Gly Ser Gly Cys Gly Gly Asp Pro
                260                 265                 270

Lys Cys Met Asp Arg Val Cys Phe Trp Arg Leu Gly Leu Leu Arg Gly
                275                 280                 285

Pro Gly Ala Glu Asp Asn Ala His Asn Glu Ile Leu Ser Asn Ala Asp
```

```
                290             295             300
Ser Leu Ser Thr Phe Val Ser Glu Gln Gln Met Glu Ser Gln Glu Pro
305                     310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Leu Leu
            340                 345                 350

Val Pro Ala Asn Gly Ala Asp Pro Thr Glu Thr Leu Met Leu Phe Phe
            355                 360                 365

Asp Lys Phe Ala Asn Ile Val Pro Phe Asp Ser Trp Asp Gln Leu Met
            370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
                420                 425                 430

Glu Arg Met Glu Glu Arg His Ala Arg Glu Lys Ile Gln Asp Leu Leu
            435                 440                 445

Val Asp Ser Gly Lys Phe Ile Tyr Leu Glu Asp Gly Thr Gly Ser Ala
            450                 455                 460

Val Ser Leu Glu
465

<210> SEQ ID NO 36
<211> LENGTH: 649
<212> TYPE: DNA
<213> ORGANISM: Artificial Sequence
<220> FEATURE:
<223> OTHER INFORMATION: synthetic anti-DR4 monoclonal antibody M921
      light chain

<400> SEQUENCE: 36
cagcctgtgc tgactcagcc accctcagcg tctgcgaccc ccggacagag ggtcaccatc    60
tcttgctctg gaagcagttc aacatcgga agtaatactt tagactggtt ccagcagctc   120
ccaggaacgg cccccaaact cctcatcttt gatactaatc ggcggccctc aggggtccct   180
gaccgattct ctggctccaa gtctggcacc tcagcctccc tggccatcag tggcctccag   240
gctgaggatg aggctgttta cttttgtgca acatgggata cagcctcaa cggcgcggtg   300 ttcggcgggg gtaccaagct cagcgtccca cgtcaggcca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca caagtacgc ggccagcagc   540 tatctgagcc tgacgcctga gcagtggaag tcccacagaa gctacagctg ccaggtcacg   600
catgaaggga gcaccgtgga agacagtg gcccctacag aatgttcat                649

<210> SEQ ID NO 37
<211> LENGTH: 720
<212> TYPE: DNA
<213> ORGANISM: Artificial Sequence
<220> FEATURE:
<223> OTHER INFORMATION: synthetic anti-DR4 monoclonal antibody M921
      heavy chain

<400> SEQUENCE: 37
```

| | |
|---|---|
| caggtacagc tgcagcagtc aggtccagga ctggtgaagc cctcgcagac cctctcactc | 60 |
| acctgtgcca tctccgggga cagtgtctct agcaacagtg ctgcttggaa ctggatcagg | 120 |
| cagtccccat cgagaggcct tgagtggctg ggaaggacat actacaggtc aagtggtat | 180 |
| aatgattatg cagtatctgt gaaaggtcga ataaccatca cccagacac atccaagaac | 240 |
| cagttctccc tgcagctgaa ctctgtgact cccgaggaca cggctgtgta ttactgtgca | 300 |
| agagacttgg gagtagcagc agctgacagc tactactact acggtatgga cgtctggggc | 360 |
| caagggacca cggtcaccgt ctcctcagcc tccaccaagg gcccatcggt cttccccctg | 420 |
| gcacctcct ccaagagcac ctctgggggc acagcggccc tgggctgcct ggtcaaggac | 480 |
| tacttccccg aaccggtgac ggtgtcgtgg aactcaggcg ccctgaccag cggcgtgcac | 540 |
| accttcccgg ctgtcctaca gtcctcagga ctctactccc tcagcagcgt ggtgaccgtg | 600 |
| ccctccagca gcttgggcac ccagacctac atctgcaacg tgaatcacaa gcccagcaac | 660 |
| accaaggtgg acaagaaagt tgggcccaaa tcttgtgaca aaactagtgg ccaggccggc | 720 |

<210> SEQ ID NO 38
<211> LENGTH: 651
<212> TYPE: DNA
<213> ORGANISM: Artificial Sequence
<220> FEATURE:
<223> OTHER INFORMATION: synthetic anti-DR4 monoclonal antibody M922
      light chain

<400> SEQUENCE: 38

| | |
|---|---|
| cagtctgtgc tgactcagcc accctcagcg tctgggaccc ccgggcagag ggtcaccatc | 60 |
| tcttgttctg gaagcagctc caacatcgga agtaatactg taaactggta ccagcagctc | 120 |
| ccaggaacgg cccccaaact cctcatctat agtaataatc agcggccctc aggggtccct | 180 |
| gaccgattct ctggctccaa gtctggcacc tcagcctccc tggccatcag tgggctccag | 240 |
| tctgaggatg aggctgatta ttactgtgca gcatgggatg acagcctgaa tggtcgcgtg | 300 |
| gtattcggcg gagggaccaa gctgaccgtc ctaggtcagc ccaaggctgc cccctcggtc | 360 |
| actctgttcc cacccctcc tgaggagctt caagccaaca ggccacact ggtgtgtctc | 420 |
| ataagtgact tctacccggg agccgtgaca gtggcctgga aggcagatag cagccccgtc | 480 |
| aaggcgggag tggagaccac cacaccctcc aaacaaagca caacaagta cgcggccagc | 540 |
| agctacctga gcctgacgcc tgagcagtgg aagtcccaca aaagctacag ctgccaggtc | 600 |
| acgcatgaag ggagcaccgt ggagaagaca gtggccccta cagaatgttc a | 651 |

<210> SEQ ID NO 39
<211> LENGTH: 701
<212> TYPE: DNA
<213> ORGANISM: Artificial Sequence
<220> FEATURE:
<223> OTHER INFORMATION: synthetic anti-DR4 monoclonal antibody M922
      heavy chain

<400> SEQUENCE: 39

| | |
|---|---|
| caggtacagc tgcagcagtc aggtccagga ctggtgaagc cctcgcagac cctctcactc | 60 |
| acctgtgcca tctccgggga cagtgtctct agcaacagtg ctgcttggaa ctggatcagg | 120 |
| cagtccccat cgagaggcct tgagtggctg ggaaggacat actacaggtc aagtggtat | 180 |
| aatgattatg cagtatctgt gaaagtcga ataaccatca cccagacac atccaagaac | 240 |
| cagttctccc tgcagctgaa ctctgtgact cccgaggaca cggctgtgta ttactgtgca | 300 |
| agagaaacag tggctgttga tgcttttgat atctgggggcc aagggacaat ggtcaccgtc | 360 |

```
tcttcagcct ccaccaaggg cccatcggtc ttccccctgg caccctcctc caagagcacc    420
tctgggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcagcgt gaatcacaag cccagcaaca ccaaggtgga caagaaagtt    660
gagcccaaat cttgtgacaa aactagtggc caggccggcc a                       701

<210> SEQ ID NO 40
<211> LENGTH: 4
<212> TYPE: PRT
<213> ORGANISM: Artificial Sequence
<220> FEATURE:
<223> OTHER INFORMATION: synthetic peptide linker

<400> SEQUENCE: 40

Gly Gly Gly Ser
1
```

ANTI-DR4 AGONIST ANTIBODIES

CROSS-REFERENCE TO RELATED APPLICATIONS

This application is the U.S. National Phase entry under 35 U.S.C. §371 and claims the benefit of International Application No. PCT/US2011/040750, filed Jun. 16, 2011, which claims the benefit of U.S. provisional application No. 61/355,349, filed Jun. 16, 2010, all of which are incorporated herein by reference in their entirety for all purposes.

FIELD OF THE INVENTION

The present invention provides antibodies and antibody fragments that specifically recognize and agonize the death receptor 4 ("DR4"). Also provided in the invention are polynucleotides and vectors that encode such molecules and host cells that harbor the polynucleotides or vectors.

REFERENCE TO SEQUENCE LISTING SUBMITTED AS TEXT FILE

This application includes a Sequence Listing as a text file named "SEQ_LISTING_859610.txt" created Dec. 11, 2012, and containing 29,332 bytes. The material contained in this text file is incorporated by reference in its entirety for all purposes.

BACKGROUND OF THE INVENTION

The tumor necrosis factor-related apoptosis-inducing ligand (TRAIL) and its receptors have emerged as promising targets for therapeutic products.[1] TRAIL is expressed on a limited number of cell types (mainly T cells, NK cells, monocytes, dendritic cells, neutrophils) in healthy people. To date, five TRAIL receptors have been identified: TRAIL-R1 (DR4), TRAIL-R2 (DR5), TRAIL-R3 (DcR1), TRAIL-R4 (DcR2) and osteoprotegerin (OPG). Of these, only DR4 and DR5 are functional receptors for TRAIL; the other receptors lack the intracellular functional death domain, and act only as decoy receptors. DR4 and DR5 are expressed in a broad range of solid tumors and hematologic malignancies. Binding of homotrimeric TRAIL to either receptor triggers a cascade of activities that leads to apoptosis.[2,3] DR4/DR5 trimerizes upon TRAIL binding,[3] and the intracellular death domains of trimerized DR4/DR5 are capable of activating caspase 8. Active caspase 8 further activates caspase 3, which digests polypeptides that maintain structural and biochemical integrity of cells.

The TRAIL-induced extrinsic apoptosis pathway is independent of p53,[4] which is a critical component of an intrinsic pathway. Conventional treatment of most tumors eventually select for tumor cells that have inactive p53, resulting in resistance to chemotherapy and radiotherapy.[5] In these cells, the intrinsic apoptosis pathway is likely diminished A number of reports have also indicated that TRAIL synergizes with conventional anticancer therapies such as irradiation and chemotherapeutic drugs[6,7,8] Importantly, TRAIL has been reported to trigger apoptosis in cancer cells while sparing normal cells.[9] The unique function of DR4/DR5 and their expression profile have made them a promising candidate for rationally-designed drugs.

Recombinant TRAIL (rTRAIL), which can induce apoptosis of cells that express DR4 or DR5, has been explored as a potential therapeutic.[10] While rTRAIL activates both DR4 and DR5, its half life is relatively short (1-2 days or less), although it can be engineered as an Fc fusion protein that has an extended half-life. It also exhibits cytotoxicity in hepatocytes and neuronal cells.[11] In combination therapies, rTRAIL has been used to sensitize previously resistant cancer cells, but it also sensitizes normal cells in some cases. Some tumor cells are protected from rTRAIL-induced apoptosis, possibly through the expression of decoy receptors. Repeated TRAIL exposure may also induce resistance to cancer cells to TRAIL therapies.[12]

An alternative approach involves targeting DR4 or DR5 with therapeutic human monoclonal antibodies (mAbs), which have a long half-life (20 days for IgG1) and tend to have low immunogenicity potential. It is not yet clear whether rTRAIL or an agonistic antibody will be the more efficacious therapy in humans; preclinical and clinical studies with both types of candidate therapeutics are in progress. Several groups have published proof-of-concept studies using murine anti-DR4/DR5 antibodies in animal models.[14,15] Preliminary animal studies have demonstrated tumor killing activities by anti-DR4/DR5 antibodies in multiple types of tumors.[13,16] Three human antibodies, anti-DR4 mapatumumab (Human Genome Sciences), anti-DR5 lexatumumab (Human Genome Sciences) and anti-DR5 conatumumab (Amgen), are in Phase 2 clinical studies, as is the humanized anti-DR5 tigatuzumab (CS-1008; Daiichi Sankyo).

Combination therapies that include anti-TRAIL receptor agonistic antibodies with other treatments such as paclitaxel, carboplatin, histone deacetylase inhibitor may provide better responses in clinical studies.[17,18] Clinical efficacy of the candidates either as a monotherapy or as part of combination therapy, and possible synergies, are currently being tested in Phase 2 and 3 studies. Additional potent human mAbs that target this pathway will find use. The present invention is based, in part, on the identification and characterization of wholly human mAbs specific for DR4.

BRIEF SUMMARY OF THE INVENTION

The present invention provides antibodies that bind to and agonize death receptor 4 ("DR4"), compositions comprising the antibodies, and methods of producing and using the antibodies. Preferably, the antibodies are monoclonal and fully human.

Accordingly, in one aspect, the invention provides antibodies that bind to the same or an overlapping epitope on death receptor 4 ("DR4") as monoclonal antibody m921. In some embodiments, the antibody competes with monoclonal antibody m921 for binding to DR4. In some embodiments, the antibodies bind to an epitope within residues 25-239 of DR4, but not within residues 77-90 of DR4. In some embodiments, the antibodies bind to a conformational epitope within residues 25-239 of DR4, but not within residues 77-90 of DR4.

In a related aspect, the invention provides antibodies that bind to the same or an overlapping epitope on death receptor 4 ("DR4") as monoclonal antibody m922, wherein the antibody is an agonist of DR4. In some embodiments, the antibody competes with monoclonal antibody m922 for binding to DR4.

In a related aspect, the invention provides antibodies that bind to and are an agonist of DR4. In some embodiments, the antibody comprises a heavy chain variable region and a light chain variable region, wherein the heavy chain variable region and the light chain variable region each comprise the following three complementary determining regions (CDRs): CDR1, CDR2 and CDR3; wherein:

i) the CDR1 of the heavy chain variable region comprises the amino acid sequence of SEQ ID NO:8;

ii) the CDR2 of the heavy chain variable region comprises the amino acid sequence of SEQ ID NO:9;

iii) the CDR3 of the heavy chain variable region comprises an amino acid sequence selected from SEQ ID NO:10 or SEQ ID NO:13;

iv) the CDR1 of the light chain variable region comprises the amino acid sequence of SEQ ID NO:5;

v) the CDR2 of the light chain variable region comprises the amino acid sequence of SEQ ID NO:31;

vi) the CDR3 of the light chain variable region comprises the amino acid sequence of SEQ ID NO:30.

In some embodiments, the antibody comprises a heavy chain variable region and a light chain variable region, wherein the heavy chain variable region and the light chain variable region each comprise the following three complementary determining regions (CDRs): CDR1, CDR2 and CDR3; wherein:

i) the CDR1 of the heavy chain variable region comprises the amino acid sequence of SEQ ID NO:8;

ii) the CDR2 of the heavy chain variable region comprises the amino acid sequence of SEQ ID NO:9;

iii) the CDR3 of the heavy chain variable region comprises an amino acid sequence selected from SEQ ID NO:10;

iv) the CDR1 of the light chain variable region comprises the amino acid sequence of SEQ ID NO:5;

v) the CDR2 of the light chain variable region comprises the amino acid sequence of SEQ ID NO:6;

vi) the CDR3 of the light chain variable region comprises the amino acid sequence of SEQ ID NO:7.

In some embodiments, the one or more of the CDR1, CDR2 or CDR3 can have one, two, three, four or five amino acid substitutions, e.g., conservative amino acid changes, while still retaining binding affinity to DR4. The altered CDRs can independently be in the heavy chain variable region and/or the light chain variable region. Amino acid positions in the CDRs that can tolerate substitution are indicated in the consensus sequences, described herein.

In some embodiments, the antibody comprises a heavy chain variable region and a light chain variable region, wherein the heavy chain variable region and the light chain variable region each comprise the following three complementary determining regions (CDRs): CDR1, CDR2 and CDR3; wherein:

i) the CDR1 of the heavy chain variable region comprises the amino acid sequence of SEQ ID NO:8;

ii) the CDR2 of the heavy chain variable region comprises the amino acid sequence of SEQ ID NO:9;

iii) the CDR3 of the heavy chain variable region comprises an amino acid sequence selected from SEQ ID NO:13;

iv) the CDR1 of the light chain variable region comprises the amino acid sequence of SEQ ID NO:5;

v) the CDR2 of the light chain variable region comprises the amino acid sequence of SEQ ID NO:11;

vi) the CDR3 of the light chain variable region comprises the amino acid sequence of SEQ ID NO:12.

In some embodiments, the antibody comprises a light chain variable segment having at least about 50%, 60%, 70%, 80%, 90%, 91%, 92%, 93%, 94%, 95%, 96%, 97%, 98%, 99% sequence identity to SEQ ID NO:33 and a heavy chain variable segment having at least about 50%, 60%, 70%, 80%, 90%, 91%, 92%, 93%, 94%, 95%, 96%, 97%, 98%, 99% sequence identity to SEQ ID NO:34. In some embodiments, the antibody comprises a light chain variable segment of SEQ ID NO:33 and a heavy chain variable segment of SEQ ID NO:34.

In some embodiments, the antibody comprises a light chain variable region having at least about 50%, 60%, 70%, 80%, 90%, 91%, 92%, 93%, 94%, 95%, 96%, 97%, 98%, 99% sequence identity to SEQ ID NO:1 and a heavy chain variable region having at least about 50%, 60%, 70%, 80%, 90%, 91%, 92%, 93%, 94%, 95%, 96%, 97%, 98%, 99% sequence identity to SEQ ID NO:2. In some embodiments, the antibody comprises a light chain variable segment of SEQ ID NO:1 and a heavy chain variable segment of SEQ ID NO:2.

In some embodiments, the antibody comprises a light chain variable region having at least about 50%, 60%, 70%, 80%, 90%, 91%, 92%, 93%, 94%, 95%, 96%, 97%, 98%, 99% sequence identity to SEQ ID NO:3 and a heavy chain variable region having at least about 50%, 60%, 70%, 80%, 90%, 91%, 92%, 93%, 94%, 95%, 96%, 97%, 98%, 99% sequence identity to SEQ ID NO:4. In some embodiments, the antibody comprises a light chain variable segment of SEQ ID NO:3 and a heavy chain variable segment of SEQ ID NO:4.

In some embodiments, the antibody is a monoclonal antibody. In some embodiments, the antibody is a human antibody. In some embodiments, the antibody is a humanized antibody.

In some embodiments, the antibody is a multivalent antibody, e.g., bivalent, trivalent, tetravalent, antibody. In some embodiments, the antibody is a multispecific antibody, such as a bispecific antibody. In some embodiments, the antibody is cross-linked.

In some embodiments, the antibody is a FAb' fragment. In some embodiments, the antibody is a single chain antibody (scFv). In some embodiments, the antibody comprises human constant regions.

In some embodiments, the antibodies do not bind to DR5.

In a related aspect, the invention further comprises compositions comprising an anti-DR4 antibody agonist of the invention, and a pharmaceutically acceptable carrier.

In a further aspect, the invention provides polynucleotides encoding an anti-DR4 antibody agonist of the invention. In some embodiments, the polynucleotide encoding the heavy chain has at least 50%, 60%, 70%, 80%, 85%, 89%, 90%, 91%, 92%, 93%, 94%, 95%, 96%, 97%, 98%, 99% or 100% nucleic acid sequence identity with a polynucleotide selected from the group consisting of SEQ ID NO:37 and SEQ ID NO:39. In some embodiments, the polynucleotide encoding the light chain has at least 50%, 60%, 70%, 80%, 85%, 89%, 90%, 91%, 92%, 93%, 94%, 95%, 96%, 97%, 98%, 99% or 100% nucleic acid sequence identity with a polynucleotide selected from the group consisting of SEQ ID NO:36 and SEQ ID NO:38.

In some embodiments, the polynucleotide encoding the heavy chain has at least 50%, 60%, 70%, 80%, 85%, 89%, 90%, 91%, 92%, 93%, 94%, 95%, 96%, 97%, 98%, 99% or 100% nucleic acid sequence identity with a polynucleotide of SEQ ID NO:37. In some embodiments, the polynucleotide encoding the light chain has at least 50%, 60%, 70%, 80%, 85%, 89%, 90%, 91%, 92%, 93%, 94%, 95%, 96%, 97%, 98%, 99% or 100% nucleic acid sequence identity with a polynucleotide of SEQ ID NO:36 (i.e., m921).

In some embodiments, the polynucleotide encoding the heavy chain has at least 50%, 60%, 70%, 80%, 85%, 89%, 90%, 91%, 92%, 93%, 94%, 95%, 96%, 97%, 98%, 99% or 100% nucleic acid sequence identity with a polynucleotide of SEQ ID NO:39. In some embodiments, the polynucleotide encoding the light chain has at least 50%, 60%, 70%, 80%, 85%, 89%, 90%, 91%, 92%, 93%, 94%, 95%, 96%, 97%, 98%, 99% or 100% nucleic acid sequence identity with a polynucleotide of SEQ ID NO:38 (i.e., m922).

In a further aspect, the invention provides expression cassettes and vectors comprising a polynucleotide encoding an anti-DR4 antibody, as described herein. The invention further provides host cells comprising the expression cassettes and vectors. The host cells can be bacterial, yeast, insect, mammalian or human host cells.

In another aspect, the invention provides methods of inducing apoptosis in a target cell expressing DR4 comprising contacting the cancer cell with an anti-DR4 antibody of the invention, as described herein. In some embodiments, the cell is in vivo. In some embodiments, the cell is in vitro. In some embodiments, the cell is a cancer cell, e.g., a cancer cell that expresses DR4.

In a related aspect, the invention provides methods of reducing, inhibiting or preventing the growth of a cancer expressing DR4 in a subject in need thereof, comprising administering to the subject a therapeutically effective amount of an antibody of any one of claims 1 to 6. In some embodiments, the methods further comprise administering to the subject an anticancer chemotherapeutic drug and/or irradiation.

In a further aspect, the invention provides kits comprising an anti-DR4 antibody of the invention, as described herein. In some embodiments, the kits comprise a second agent for co administration with the antibody. In some embodiments, the kits further comprise a second anti-DR4 antibody that binds to a non-overlapping epitope of DR4. In some embodiments, the kits further comprise an anti-DR5 antibody. In some embodiments, the kits further comprise an antineoplastic agent.

DEFINITIONS

The term "death receptor 4" or "DR4" refer to TNFRSF10A tumor necrosis factor receptor superfamily, member 10a (also known as APO2; CD261; MGC9365; TRAILR1; and TRAILR-1). DR4 is a member of the TNF-receptor superfamily, is activated by tumor necrosis factor-related apoptosis inducing ligand (TNFSF10/TRAIL), and transduces cell death signal and induces cell apoptosis. Studies with FADD-deficient mice suggested that FADD, a death domain containing adaptor protein, is required for the apoptosis mediated by this protein. The nucleic acid and amino acid sequences of human DR4 are recorded, e.g., as GenBank Accession Nos. NM_003844.3 → NP_003835.3, respectively.

The terms "agonist" and "agonistic" when used herein refer to or describe a molecule which is capable of, directly or indirectly, substantially inducing, promoting or enhancing DR4 biological activity or activation. Optionally, an "agonist DR4 antibody" is an antibody which has activity comparable to the ligand for DR4, known as Apo-2 ligand (TRAIL), or is capable of activating DR4 receptor which results in an activation of one or more intracellular signalling pathways which may include activation of caspase 3, caspase 8, caspase 10 or FADD.

"Antibodies" exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to VH—CH by a disulfide bond. The F(ab)'$_2$ may be reduced under mild conditions to break the disulfide linkage in the hinge region thereby converting the (Fab)$_2$ dimer into a Fab' monomer. The Fab' monomer is essentially a Fab with part of the hinge region (see, W. E. Paul, ed., Fundamental Immunology, Raven Press, N.Y. (1993), for a more detailed description of these and other antibody fragments). While various antibody fragments are defined in terms of the digestion of an intact antibody, one of skill will appreciate that such Fab' fragments may be synthesized de novo either chemically or by utilizing recombinant DNA methodology.

For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. IgG$_1$, IgG$_2$, IgG$_3$ or IgG4), IgD, IgA or IgE). In some embodiments, the antibody is an isotype human IgG1, for example, an isotype human IgGγ1.

The term "antibody fragments" means molecules that comprise a portion of an intact antibody, generally the antigen binding or variable region of the intact antibody. Examples of antibody fragments include Fab, Fab', F(ab')2, and Fv fragments; helix-stabilized antibodies (see, e.g., Arndt et al., J Mol Biol 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11): 484-490 (2003), Ghahroudi et al., FEBS Lett. 414:521-526 (1997), Lauwereys et al., EMBO J. 17:3512-3520 (1998), Reiter et al., J. Mol. Biol. 290:685-698 (1999), Davies and Riechmann, Biotechnology, 13:475-479 (2001)).

As used herein, the term "anti-DR4" in reference to an antibody, includes reference to an antibody which is generated against DR4. The DR4 generally is a mammalian DR4. In some embodiments, the DR4 is a primate DR4, for example, human DR4. In one embodiment, the antibody is generated against human DR4 synthesized by a non-primate mammal after introduction into the animal of cDNA which encodes human DR4. The antibodies can be cross-reactive with DR4proteins from different mammalian species, e.g., human, mouse, non-human primate.

The term "diabodies" refers to small antibody fragments with two antigen-binding sites, which fragments comprise a variable heavy domain ("V$_H$" or "VH") connected to a variable light domain ("V$_L$" or "VL") in the same polypeptide chain (V$_H$—V$_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Holliger et al., Proc. Natl. Acad. Sci. USA, 90: 6444-6448 (1993).

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. (see, Kabat, E., et al., SEQUENCES OF PROTEINS OF IMMUNOLOGICAL INTEREST, U.S. Department of Health and Human Services, (1987), which is hereby incorporated by reference). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

An antibody that binds to the "same epitope" competes for binding with the reference antibody on the target polypeptide (e.g., DR4). Therefore, antibodies having the same epitope may have identical or overlapping epitopes. Competition assays are used for determining whether antibodies compete for the same epitope are known in the art, and described herein. For example, an ELISA assay format can be used to determine if two antibodies bind to or compete for the same epitope. The first antibody is held at a constant concentration, while the second antibody is contacted to the target antigen in the presence of the first antibody at several different concentration. If concurrent binding of both antibodies can be detected, they do not have the same epitope. If the first or the second antibody binds to the target antigen, then the antibodies compete with each other for binding to the target antigen, and as the term is used herein, bind to the same epitope. In some embodiments, a reference antibody and a test antibody are tested to determine if they concurrently bind to or exclusively bind to residues 25-239 of DR4.

References to "VH" or a "$V_H$" refer to the variable region of an immunoglobulin heavy chain, including an Fv, scFv, dAb, dsFv or Fab. References to "VL" or a "$V_L$" refer to the variable region of an immunoglobulin light chain, including of an Fv, scFv, dsFv, dAb, or Fab.

The term "Fv" refers to the variable domains of the heavy chain and of the light chain of an antibody. The phrase "single chain Fv" or "scFv" refers to an antibody in which the variable domains of the heavy chain and of the light chain of a traditional two chain antibody have been joined to form one chain. Optionally, a linker (usually a peptide) is inserted between the two chains to allow for proper folding and creation of an active binding site. If a linker is present, it is excluded for purposes of comparing the percentage of sequence identity between a given VH or VL chain and a VH or VL chain of the m921 or the m922 antibodies.

Antibodies of the invention include multispecific antibodies. Multispecific antibodies have more than one binding specificity. In the present invention, at least one binding site of such multispecific antibodies has the binding specificity, i.e., binds to the same epitope, as the m921 or m922 antibody. In some embodiments, at least one binding site of a multi-specific antibody has the heavy chain CDRs and/or light chain CDRs of the m921 or m922 antibody. The term "bispecific" antibody as used herein refers to an antibody that has at two binding sites each of which bind to different epitopes of the same antigen or a different antigen.

The term "valent" as used herein refers to a specified number of binding sites in an antibody molecule. A "multivalent" antibody has two or more binding sites. Thus, the terms "bivalent", "trivalent", and "tetravalent" refers to the presence of two binding sites, three binding sites, and four binding sites, respectively. A bispecific antibody according to the invention is at least bivalent and may be trivalent, tetravalent, or otherwise multivalent. Multispecific antibodies of the invention, e.g., bispecific antibodies, include, for example, multivalent single chain antibodies, diabodies and triabodies, as well as antibodies having a constant domain structure such as that of full length antibodies, to which further antigen-binding sites (e.g., single chain Fv, a $V_H$ domain and/or a $V_L$ domain, Fab, or (Fab)$_2$) are linked, typically via one or more peptide linkers.

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The antibodies of the present invention can be encoded by nucleic acid sequences that correspond to a human germline sequence. The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other evaluated variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementary determining regions only, framework and complementary determining regions, a variable segment, or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 94%, 96%, 98%, 99% sequence identity with the reference variable region nucleic acid or amino acid sequence. Corresponding human germline sequences can be determined, for example, through the publicly available international ImMunoGeneTics database (IMGT) (on the worldwide web at imgt.cines.fr/) and V-base (on the worldwide web at vbase.mrc-cpe.cam.ac.uk).

The term "linker peptide" includes reference to a peptide within an antibody binding fragment (e.g., Fv fragment) which serves to indirectly bond the variable domain of the heavy chain to the variable domain of the light chain.

A "targeting moiety" is the portion of an immunoconjugate intended to target the immunoconjugate to a cell of interest. Typically, the targeting moiety is an antibody, a scFv, a dsFv, an Fab, or an F(ab')$_2$.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as antineoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The terms "chimeric molecule" and "immunoconjugate" refer to linkage of an antibody to an effector moiety. The linkage is usually a covalent bond between the effector moiety and the antibody. The linkage can be by chemical conjugation, or by expressing the antibody and the effector moiety from a nucleic acid encoding both the antibody and the effector moiety. For example, a nucleic acid encoding an m921 or m922 antibody of the invention fused to a *Pseudomonas* exotoxin can be recombinantly expressed in *E. coli* and then isolated.

The terms "effective amount" or "amount effective to" or "therapeutically effective amount" includes reference to a dosage of a therapeutic agent sufficient to produce a desired result, such as inhibiting cell protein synthesis or tumor growth by at least 50%, or killing the cell.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "connected to," in relation to an antibody and a therapeutic moiety or detectable label, means that the antibody is fused to (e.g., by recombinant expression) or conjugated to (e.g., chemically attached to) the therapeutic moiety or detectable label, directly or through a linker.

The term "contacting" includes reference to placement in direct physical association.

An "expression plasmid" comprises a nucleotide sequence encoding a molecule or interest, which is operably linked to a promoter.

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins: Structures and Molecular Properties*, W. H. Freeman and Company, New York (2nd Ed., 1992).

The terms "substantially similar" in the context of a peptide indicates that a peptide comprises a sequence with at least 90%, for example at least 95%, sequence identity to the reference sequence (e.g., SEQ ID NOs:1-34) over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (*Proc. Nat'l Acad. Sci. USA* 82:2306-2309 (1985), or the ciliate *Macronucleus*, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, for example at least 80%, or at least 90-95% nucleotide or amino acid residue identity, when compared and aligned for maximum correspondence, as measured using one of the following sequence comparison algorithms or by visual inspection. The substantial identity can exist over a region of the sequences that is at least about 50 residues in length, for example, over a region of at least about 100 residues, or over at least about 150 residues. In one embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (on the internet by entering "www." followed by "ncbi.nlm.nih.gov/"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (e.g., SEQ ID NOS:36-39) if the smallest sum probability in a comparison of the test nucleic acid to the reference nucleic acid is less than about 0.1, for example less than about 0.01, or less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, non-human primates, rats, mice, hamsters, guinea pigs, chimpanzees, or macaques. The cells may be cultured in vivo or in vitro.

The term "selectively reactive" or "specifically binds" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, for example greater than 5-fold, or greater than 10-fold and can result in greater than 100-fold increase in amount of bound antibody (per unit time) to a cell or tissue bearing DR4 as compared to a cell or tissue lacking DR4. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods of the present invention are generally "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to administration of an anti-DR4 antibody or antibody fragment. In some embodiments, the growth, progression or spread of a tumor or cancer is inhibited, reduced or decreased by at least about 1-fold, 2-fold, 3-fold, 4-fold, or more in comparison to the tumor burden prior to administration of an anti-DR4 antibody or antibody fragment.

The term "co-administered" refers to two active pharmacological agents in the blood or body tissues of a host at the same time. Co-administered agents can be concurrently administered, or sequentially administered.

Compositions or methods "comprising" one or more recited elements may include other elements not specifically recited. For example, a composition that comprises the VH and VL CDR sequences of the invention encompasses both the CDRs and the variable regions, antibodies and antibody fragments comprising the CDRs.

Compositions or methods "consisting essentially of" one or more recited elements include the elements specifically recited and may further include pharmacologically inactive components (e.g., excipients, vehicles), but do not include unrecited pharmacologically active agents.

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, annexin V binding assays, PARP assays, FACS analysis or DNA electrophoresis, all of which are known in the art. Optionally, apoptotic activity will be determined by way of an annexin V or PARP assay.

The terms "cancer," "cancerous," and "malignant" refer to or describe the physiological condition in mammals that is typically characterized by unregulated cell growth. Examples of cancer include but are not limited to, carcinoma, including adenocarcinoma, lymphoma, blastoma, melanoma, glioma, sarcoma, myeloma (such as multiple myeloma) and leukemia. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, Burkitt's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer.

DETAILED DESCRIPTION

1. Introduction

Figure 1A:
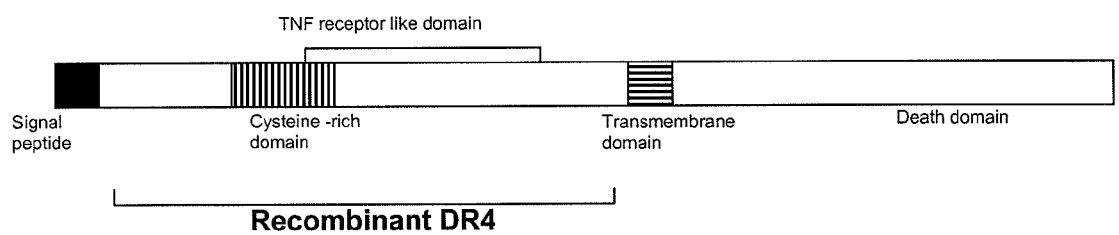
FIG. 1. Selection of DR4-specific antibodies from human phage-displayed Fab library. A, Diagram of the recombinant DR4 protein used for selection. B, In vitro binding of the two selected antibodies to DR4. -■-, m921 IgG; -♦-, m922 IgG. The two IgGs were 1:5 serially diluted from 1000 nM to 0.0128 nM.

The tumor necrosis factor-related apoptosis-inducing ligand (TRAIL) and its functional receptors, DR4 and DR5, have been established as promising targets for cancer treatment. Therapeutics targeting TRAIL and its receptors are not only effective in killing many types of tumors, but they also synergize with traditional therapies and show efficacy against tumors that are otherwise resistant to conventional treatments. The present invention is based, in part, on the identification and characterization of two human monoclonal antibodies, m921 and m922, that are specific for human DR4. Both antibodies competed with TRAIL for binding to DR4. The anti-DR4 agonistic antibodies described herein find use as anticancer therapeutics and in detecting expression of DR4 protein expression.

The present invention demonstrates the successful isolation from a phase display of human Fab which recognize DR4. The antibodies described herein bind strongly and to DR4 expressed on target cells, e.g., cancer cells. The anti-DR4 human antibodies stimulate intracellular signaling through DR4 and induce or promote apoptosis of the DR4-expressing target cells. The anti-DR4 agonistic antibodies can be cross-linked or multivalent, or can be used as a targeting moiety in an immunotoxin. The fully human anti-DR4 antibodies described herein find use in the treatment and prevention of cancers that express or overexpress DR4, particularly solid cancers, including without limitation, lung cancer, renal cancer, cervical cancer, lymphomas (e.g., Burkitt's lymphoma), myelomas, and colorectal cancers.

Due to their low immunogenicity in human patients, fully human mAb are the most desirable antibody format for clinical application (Huls, et al., *Nat Biotechnol* (1999) 17:276-81). The present invention provides agonistic anti-DR4 antibodies and antibody fragments (exemplified by m921 and m922) that are specific for tumor-associated DR4. Anti-DR4 human antibodies can be isolated from a human phage display libraries (e.g., Fab, scFv) and converted into intact, fully human mAb, e.g., an IgG1 mAb. The antibodies described herein bind specifically to cell surface-associated DR4 on cancer cells with high affinity and kill cancer cells, e.g., by inducing or promoting apoptosis or programmed cell death of the target cell. Furthermore, immuntoxins that utilize the present antibodies as a targeting moiety kill DR4-expressing cancer cells with high cytotoxic activity.

The antibodies described herein have the advantage of being created from human germline sequences. The present antibodies can therefore be wholly human and elicit reduced or no immunogenic response when administered to a human. In the context of treatment, the antibodies of the invention can be used alone, to promote or induce apoptosis, or as a targeting moiety in an immunotoxin. Immunotoxins are chimeric proteins composed of an antibody or antibody fragment moiety and an effector or therapeutic moiety. The present antibodies find use to target an effector or therapeutic moiety, including drugs (e.g., antineoplastic or chemotherapeutic drugs, as described herein), liposomes loaded with a drug, radionuclides or cytotoxins to cells which express DR4 on their exterior surface. The present antibodies also find use as reagents for diagnosis, prognosis and detection, for example, in immunohistochemistry and immunoassays. The antibodies provided herein have very high affinity for DR4. For example, EC50s for both the m921 and m922 antibodies are about 10 nM, wherein EC50 is the concentration in an ELISA assay for 50% binding.

Further, the antibodies can be prepared and used as fragments, such as Fabs, that retain antigen recognition that can be used as the targeting portion of immunoconjugates. Alternatively, the Fv regions of the antibodies can be recombinantly produced in frame with a toxin moiety to produce the chimeric molecules known as immunotoxins. Typically, immunotoxins for treatment of solid tumors use single chain Fv regions ("scFvs") or disulfide stabilized Fv regions ("dsFvs") since the Fv regions are significantly smaller than whole immunoglobulins, which permits the immunotoxin to better penetrate into the tumor.

The antibodies described herein can be modified without changing their ability to be used for the purposes described above. The antibodies thus have framework regions (regions outside the complementarity determining regions, or "CDRs") and CDRs which are wholly human. Accordingly, the anti-DR4 antibodies provided herein are preferred for in vivo use, since they have a lower risk of inducing side effects and typically can remain in the circulation longer. Moreover, the framework regions can be altered using methods known in the art, e.g., to another human framework sequence or a framework sequence from another mammalian species, as desired. Since the CDRs of the variable regions determine antibody specificity, the CDRs of the anti-DR4 antibodies described herein can be grafted or engineered into an antibody of choice to confer specificity for DR4 upon that antibody.

2. Anti-DR4 Antibodies

In some embodiments, the invention provides anti-DR4 antibodies which have CDRs 1, 2, and 3 of the $V_H$ chain (i.e., SEQ ID NOs:8, 9 and 10 or 13, respectively) and CDRs 1, 2, and 3 of the $V_L$ chain (i.e., SEQ ID NOs:5, 31 and 32, respectively). In some embodiments, the invention provides anti-DR4 antibodies which have CDRs 1, 2, and 3 of the $V_H$ chain (i.e., SEQ ID NOs:8, 9 and 10, respectively) and CDRs 1, 2, and 3 of the $V_L$ chain (i.e., SEQ ID NOs:5, 6 and 7, respectively). In some embodiments, the invention provides anti-DR4 antibodies which have CDRs 1, 2, and 3 of the $V_H$ chain (i.e., SEQ ID NOs:8, 9 and 13, respectively) and CDRs 1, 2, and 3 of the $V_L$ chain (i.e., SEQ ID NOs:5, 11 and 12, respectively). In some forms, the anti-DR4 antibodies are Fab. In some forms, the VH and VL chains will be linked by a peptide linker, to form a scFv, or may have one or more cysteine residues engineered into the framework region to permit formation of a disulfide bond linking the two chains together. In some forms, the anti-DR4 antibodies.

Because of the multiplicity of forms in which the variable regions of the m921 and the m922 antibodies can be expressed, and to the variants of the antibodies which can be made, for convenience of reference, the discussion herein will sometimes refer to "m921 antibodies" or "m922 antibodies". M921 antibodies or antibody fragments comprise CDRs 1, 2, and 3 of the $V_H$ chain (i.e., SEQ ID NOS:8, 9 and 10, respectively) and CDRs 1, 2, and 3 of the $V_L$ chain (i.e., SEQ ID NOS:5, 6 and 7, respectively). M922 antibodies or antibody fragments comprise CDRs 1, 2, and 3 of the $V_H$ chain (i.e., SEQ ID NOS:8, 9 and 13, respectively) and CDRs 1, 2 and 3 of the $V_L$ chain (i.e., SEQ ID NOS:5, 11 and 12, respectively).

It is contemplated that the m921 and m922 antibodies can be modified in various ways without losing antigen recognition capability. The consensus sequences provided herein identify residues that will tolerate substitution. Thus, the invention provides antibodies which specifically bind DR4 and which have $V_H$ chains with at least 90%, 93%, 95%, 97% or 99% amino acid sequence identity to the sequence of the $V_H$ chain of the m921 antibody (SEQ ID NO:2) and/or $V_L$ chains with at least 90%, 93%, 95%, 97% or 99% amino acid sequence identity to the sequence of the $V_L$ chain of the m921 antibody (SEQ ID NO:1). In some embodiments, the invention provides antibodies which specifically bind DR4 and which have $V_H$ chains with 100% sequence identity to the sequence of the $V_H$ chain of the m921 antibody (SEQ ID NO:2) and/or $V_L$ chains with 100% sequence identity to the sequence of the $V_L$ chain of the m921 antibody (SEQ ID NO:1).

The invention further provides antibodies which specifically bind DR4 and which have $V_H$ chains with at least 90%, 93%, 95%, 97% or 99% amino acid sequence identity to the sequence of the $V_H$ chain of the m922 antibody (SEQ ID NO:4) and/or $V_L$ chains with at least 90%, 93%, 95%, 97% or 99% amino acid sequence identity to the sequence of the $V_L$ chain of the m922 antibody (SEQ ID NO:3). In some embodiments, the invention provides antibodies which specifically bind DR4 and which have $V_H$ chains with 100% sequence identity to the sequence of the $V_H$ chain of the m922 antibody (SEQ ID NO:4) and/or $V_L$ chains with 100% sequence identity to the sequence of the $V_L$ chain of the m922 antibody (SEQ ID NO:3).

Preferably, the antibodies have a binding constant ($K_D$) that is about 100 nM or less, for example in the range of about 1-100 nM, for example, about 100 nM, 75 nM, 50 nM, 25 nM, 10 nM, 5 nM, 3 nM, 2 nM, 1 nM, or less. Affinity can be measured using any method known in the art. Applicable assays are described herein, e.g., BIAcore analysis. Another applicable assay is provided in U.S. Patent Publication 2009/0047211. Whether or not a modified antibody retains this utility can be readily determined by, for example, conducting one of these tests with the modified antibody and comparing the results to the results of a like test conducted using the m921 or the m922 antibody.

The CDRs of the m921 and m922 antibodies can also be modified to improve their affinity. Work from the laboratory of the present inventors has established that the affinity of antibodies can be improved by mutating residues encoded by codons in mutational "hotspots," which are nucleotide sequences where mutations are frequently concentrated during the in vivo affinity maturation process. Mutation of residues encoded by a codon with nucleotides within one of two consensus sequences is particularly useful. The two consensus sequences are (1) a tetranucleotide A/G-G-C/T-A/T (Pu-G-Py-A/T), and the serine codons AGY, where Y can be a C or a T (see, Wagner et al., Nature, 376:732 (1995); and Goyenechea and Milstein, Proc. Natl. Acad. Sci. USA 93:13979-13984 (1996)). The technique for mutating hotspots and selecting antibodies with increased affinity compared to the starting antibody (sometimes called the "parental" antibody) is explained in detail in, for example, PCT/US00/14829, International Publication No. WO 00/73346. Thus, it is contemplated that the affinity of the m921 or the m922 antibody, or both, can be improved by mutating residues in their CDRs, which residues are encoded by codons in one of the two consensus hotspot motifs set forth above. For convenience of reference, such residues can be referred to as "hot spot residues".

It is also noted that making a conservative substitution of a CDR residue encoded by a codon whose nucleotides are not within a hot spot motif can often be made without markedly changing the affinity of the resulting antibody (for convenience, such a residue can be referred to as a "non-hot spot residue"). Persons of skill will therefore recognize that antibodies having a CDR with, for example, a single non-hot spot residue mutation compared to the CDRs set forth herein for the m921 or the m922 antibody, which have affinities close to those reported for the m921 or the m922 antibody, and which have similar efficacy in immunotherapy, immunological assays and immunohistochemical techniques, can be used in the methods of the invention. For purposes of determining whether an antibody has an affinity close to that reported for the m921 or the m922 antibody but in which one or more CDRs have a single non-hot spot residue mutations can be considered to have an affinity close to that reported for the m921 or the m922 antibody if its affinity is within 1 nM of that reported herein for the corresponding antibody (e.g., to that of the m921 antibody if the CDRs are those of the m922 antibody except for the mutation of the non-hot spot residue and, optionally, of a hot spot residue). For purposes of determining whether an antibody has similar efficacy in immunotherapy, immunological assays and immunohistochemical techniques to that reported herein for the m921 or the m922 antibody but in which one or more CDRs have a single non-hot spot residue mutation can be considered to have an affinity close to that reported for the m921 or the m922 antibody if its affinity is within 1 nM of that reported for the corresponding antibody.

It is expected that some of the antibodies made by mutating residues in hot spots in the CDRs of the m921 or the m922 antibodies will have affinities higher than that of the starting antibody. It is not expected that the affinity of these yet-higher affinity antibodies will reach zero, which would reflect a covalent bond between the antibody and the antigen.

The affinities of the m921 antibody and of the m922 antibody are quite good: the EC50s for both antibodies are about 10 nM, wherein the EC50 is the concentration in an ELISA assay for 50% binding. It is therefore expected that forms of these antibodies in which hot spot residues are mutated can be expected to have affinities stated in tenths of a nM. For purposes of being able to state a lower limit on the affinity on the mutated antibodies, the limit may be stated as 0.05 nM.

The sequences of $V_H$ and $V_L$ chains comprising CDRs 1, 2, and 3 of the $V_H$ and CDRs 1, 2, and 3 of the $V_L$ chain of the m921 antibody, or which have CDRs 1, 2, and 3 of the $V_H$ and CDRs 1, 2, and 3 of the $V_L$ chain of the m922 antibody, can also be used as the Fv regions of intact immunoglobulins. Persons of skill are aware that the Fc region of antibodies of different classes, or isotypes (IgG, IgA, IgM, etc.), is relatively invariant, and that the specificity of, for example, an IgG molecule, can be altered by engineering into the IgG a selected Fv region. Accordingly, by grafting onto the Fc region an Fv region or Fv regions of the invention (such as those comprising CDRs 1, 2, and 3 of the $V_H$ and CDRs 1, 2, and 3 of the $V_L$ chain of the m921 antibody or which have CDRs 1, 2, and 3 of the $V_H$ and CDRs 1, 2, and 3 of the $V_L$ chain of the m922 antibody), specificity and affinity for DR4 can be conferred to the immunoglobulin molecule.

The $V_L$ and $V_H$ chains of each antibody can be modified by engineering cysteines into the sequence to facilitate formation of disulfide bonds between the chains of the respective antibodies. A light chain and heavy chain of the variable region of an antibody joined by a disulfide bond between cysteines engineered into the framework region is known as a disulfide-stabilized Fv, or "dsFv." Formation of dsFvs is taught in, for example, Pastan, U.S. Pat. No. 6,558,672, which sets forth a series of positions at which cysteines can be engineered into the framework region to facilitate formation of disulfide bonding between the chains, as well as in FitzGerald et al., International Publication Number WO 98/41641. Materials and methods for constructing dsFvs are set forth in, for example, Kreitman et al., Clin. Cancer Res 6:1476-1487 (2000) and Kreitman et al., Intl J Cancer 81:148-155 (1999). These methods can be used for generation of dsFvs of the m921 and m922 antibodies. Typically, the two chains are expressed from separate plasmids in inclusion bodies in a prokaryotic host cell, such as K coli, and allowed to bond before the protein is purified from the inclusion bodies.

The antibodies of the present invention can also be used to form "chimeric antibodies" comprising the variable domains of the antibodies. The term "chimeric antibody" is used in the art to refer to an engineered antibody construct comprising variable domains of one species (such as mouse, rat, goat, sheep, cow, llama or camel variable domains), which may be humanized or not, and constant domains of another species (such as non-human primate or human constant domains) (for review see Hurle and Gross, Curr. Opin. Biotech. 5:428-433 (1994)). It should be clear that any method known in the art to develop chimeric antibodies or antibody constructs can be used. The present invention also concerns a diabody comprising a variable domain (including one which has been humanized) of an antibody of the invention. The term "diabody" relates to two non-covalently-linked scFv's, which then form a so-called diabody, as described in detail by Holliger et al. Proc. Natl. Acad. Sci. USA 90:6444 (1993) and reviewed by Poljak Structure 2:1121-1123 (1994). It should be clear that any method to generate diabodies, as for example described by these references and by Zhu et al. Biotechnology 14:192-196 (1996), can be used.

In general, even if intact immunoglobulins are made using Fvs of the invention, use of fragments of the intact immunoglobulins that retain antigen recognition, such as an Fab, an Fab', a scFv, a dsFv, or a diabody, is preferred. Many of the recombinant immunotoxins produced from constructs of scFv are one-third the size of IgG-toxin chemical conjugates and are homogeneous in composition. Elimination of the constant portion of the IgG molecule from the scFv results in faster clearance of the immunotoxin after injection into animals, including primates, and the smaller size of the conjugates improves drug penetration in solid tumors. Together, these properties lessen the side effects associated with the toxic moiety by reducing the time in which the immunotoxin (IT) interacts with non-target tissues and tissues that express very low levels of antigen.

These advantages, however, are offset to some degree by the loss of antigen binding affinity that occurs when IgGs, for example, are converted to scFvs (Reiter et al., Nature Biotechnol. 14:239-1245 (1996)). Increasing affinity has been shown to improve selective tumor delivery of scFvs (Adams et al., Cancer Res. 58:485-490 (1998)), and is likely to increase their usefulness in tumor imaging and treatment. The affinity of the antibodies of the invention, however, is so high that immunoconjugates based on these antibodies are effective in delivering effector molecules to their intended targets. The high affinity of the antibodies of the invention is therefore important and provides an alternative to the use of other high affinity anti-DR4 antibodies for delivering agents to cells expressing DR4, providing the practitioner with more flexibility in the choice of targeting moieties in fashioning immunoconjugates.

Accordingly, in some embodiments, the anti-DR4 antibody is a recombinant antibody such as a scFv or a disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In one embodiment, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. In one embodiment, the scFv is recombinantly produced. The CDRs of the $V_H$ and $V_L$ regions are as set forth herein for antibody m921 and for antibody m922. Further embodiments of the antibodies are as described herein. One of skill will realize that conservative variants of the antibodies of the instant invention can be made. Such conservative variants employed in scFv fragments will retain critical amino acid residues necessary for correct folding and stabilizing between the $V_H$ and the $V_L$ regions.

In some embodiments of the present invention, the scFv antibody is directly linked to an effector molecule ("EM") through the light chain. However, scFv antibodies can be linked to the EM via its amino or carboxyl terminus.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., *Proc. Nat'l Acad. Sci. USA* 8:5879 (1988); Bird, et al., *Science* 242:4236 (1988); Glockshuber, et al., *Biochemistry* 29:1362 (1990); U.S. Pat. Nos. 4,946,778, 5,132,405 and Stemmer, et al., *Biotechniques* 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, usually no more than 30 amino acids, for example, no more than 20 amino acids in length. In some embodiments, the peptide linker is a concatamer of the sequence Gly-Gly-Gly-Ser (SEQ ID NO:40), for example, about 2, 3, 4, 5, or 6 such sequences. However, it is to be appreciated that some amino acid substitutions within the linker can be made. For example, a valine can be substituted for a glycine.

Methods of making scFv antibodies have been described. See, e.g., Ward, et al. *Nature* 341:544-546 (1989). In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury, et al., *Mol. Immunol.* 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes.

In one embodiment, scFvs are chosen through a phage display library. The procedure described above for synthesizing scFv is followed. After amplification by PCR, the scFv nucleic acid sequences are fused in frame with gene III (gIII) which encodes the minor surface protein gIIIp of the filamentous phage (Marks, et al., *J. Biol. Chem.* 267:16007-16010 (1992); Marks, et al., *Behring Inst. Mitt.* 91:6-12 (1992); and Brinkmann, et al., *J. Immunol. Methods* 182:41-50 (1995)). The phage express the resulting fusion protein on their surface. Since the proteins on the surface of the phage are functional, phage bearing DR4-binding antibodies can be separated from non-binding or lower affinity phage by panning or antigen affinity chromatography (McCafferty, et al., *Nature* 348:552-554 (1990)).

scFv that specifically bind to DR4 are typically found by panning. Panning is done by coating a solid surface with DR4 and incubating the phage on the surface for a suitable time under suitable conditions. The unbound phage are washed off the solid surface and the bound phage are eluted. Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that bind to DR4 coated plates are expanded in *E. coli* and subjected to another round of panning. In this way, an enrichment of 2000-fold occurs in 3 rounds of panning. Thus, even when enrichment in each round is low, multiple rounds of panning will lead to the isolation of rare phage and the genetic material contained within which encodes the sequence of the highest affinity antibody. The physical link between genotype and phenotype provided by phage display makes it possible to test every member of a cDNA library for binding to antigen, even with large libraries of clones.

In some embodiments, an anti-DR4 antibody of the invention is a bispecific antibody. Bispecific anti-DR4 antibodies of the invention can be produced by any technique known in the art. For example, bispecific antibodies can be produced recombinantly using the co-expression of two immunoglobulin heavy chain/light chain pairs. See, e.g., Milstein et al., *Nature* 305: 537-39, 1983. Alternatively, bispecific antibodies can be prepared using chemical linkage. See, e.g., Brennan, et al., *Science* 229: 81, 1985. Bispecific antibodies can also be prepared by disulfide exchange; or by using recombinant expression techniques to produce a single polypeptide chain comprising two or more antibody binding sites, or to produce more than one polypeptide chain that can associate covalently to produce a bispecific antibody. A bispecific antibody can also be made entirely by chemical synthesis. A bispecific antibody may comprise two different constant regions or may be in a format that lacks constant regions. Methods of generating multispecific and multivalent antibodies are described, e.g., in WO 94/04690; Suresh et al., *Methods in Enzymology*, 121:210 (1986); Shalaby et al., *J. Exp. Med.*, 175: 217-225 (1992); Kostelny et al., *J. Immunol*, 148 (5): 1547-1553 (1992). Hollinger et al, *Proc. Natl. Acad. Sci. USA*, 90:6444-6448 (1993); Gruber et al, *J. Immunol*, 152: 5368 (1994); Tutt et al *J. Immunol.* 147: 60 (1991); WO/2010/145793; WO/2010/145792; and WO/2011/039126.

The antibodies of this invention bind to DR4 with an affinity at least that of m921 or of m922. Binding affinity for a target antigen is typically measured or determined by standard antibody-antigen assays, such as competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is <1 μM, preferably <100 nM or <10 nM, and most preferably <0.1 nM. Antibody molecules will typically have a $K_D$ in the lower ranges. $K_D=[Ab-Ag]/[Ab][Ag]$ where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible non-covalent associations such as electrostatic attraction, Van der Waals forces and hydrogen bonds. This method of defining binding specificity applies to single heavy and/or light chains, CDRs, fusion proteins or fragments of heavy and/or light chains, that are specific for DR4 if they bind DR4 alone or in combination.

The antibodies can be detected and/or quantified using any of a number of well recognized immunological binding assays (see, e.g., U.S. Pat. Nos. 4,366,241; 4,376,110; 4,517,288; and 4,837,168). For a review of the general immunoassays, see also METHODS IN CELL BIOLOGY, VOL. 37, Asai, ed. Academic Press, Inc. New York (1993); BASIC AND CLINICAL IMMUNOLOGY 7TH EDITION, Stites & Ten, eds. (1991). Immunological binding assays (or immunoassays) typically utilize a ligand (e.g., DR4) to specifically bind to and often immobilize an antibody. The antibodies employed in immunoassays of the present invention are discussed in greater detail supra.

Immunoassays also often utilize a labeling agent to specifically bind to and label the binding complex formed by the ligand and the antibody. The labeling agent may itself be one of the moieties comprising the antibody/analyte complex, i.e., the anti-DR4 antibody. Alternatively, the labeling agent may be a third moiety, such as another antibody, that specifically binds to the antibody/DR4 protein complex.

In one aspect, a competitive assay is contemplated wherein the labeling agent is a second anti-DR4 antibody bearing a label. The two antibodies then compete for binding to the immobilized DR4. Alternatively, in a non-competitive format, the DR4 antibody lacks a label, but a second antibody specific to antibodies of the species from which the anti-DR4 antibody is derived, e.g., murine, and which binds the anti-DR4 antibody, is labeled.

Other proteins capable of specifically binding immunoglobulin constant regions, such as Protein A or Protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111:1401-1406 (1973); and Akerstrom, et al., *J. Immunol.* 135:2589-2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting anti-DR4 antibodies in a sample containing the antibodies generally comprises the steps of contacting the sample with an antibody which specifically reacts, under immunologically reactive conditions, to the DR4/antibody complex.

In some embodiments, the antibodies or antibody fragments of the invention are fully human, i.e., are encoded by nucleic acids that correspond to a human germline sequence. Techniques for producing human monoclonal antibodies are known in the art, and described, e.g., in Lonberg, *Handb Exp Pharmacol* (2008) 181:69-97; Lonberg, *Curr Opin Immunol* (2008) 20(4):450-9; Lanzavecchia, et al., *Curr Opin Biotech* (2007) 18(6):523-8; and Weiner, *J Immunother* (2006) 29(1): 1-9. Anti-DR4 monoclonal human antibodies can be isolated by screening phage displays from libraries of variable region heavy and light chains encoded by nucleic acid sequences that correspond to human germline sequences for heavy and light chain combinations that bind to DR4, as described herein.

3. Immunoconjugates Comprising Anti-DR4 Antibodies

The anti-DR4 antibodies of the invention can be linked to effector molecules (EM) through the EM carboxyl terminus, the EM amino terminus, through an interior amino acid residue of the EM such as cysteine, or any combination thereof. Similarly, the EM can be linked directly to heavy, light, Fc (constant region) or framework regions of the antibody. Linkage can occur through the antibody's amino or carboxyl termini, or through an interior amino acid residue. Further, multiple EM molecules (e.g., any one of from 2-10) can be linked to the anti-DR4 antibody and/or multiple antibodies (e.g., any one of from 2-5) can be linked to an EM. The antibodies used in a multivalent immunoconjugate composition of the present invention can be directed to the same or different DR4 epitopes.

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various antineoplastic agents, cytotoxins, such as native or modified *Pseudomonas* exotoxin or Diphtheria toxin, encapsulating agents, (e.g., liposomes) which themselves contain antineoplastic agents, radioactive agents such as $^{125}$I, $^{32}$P, $^{14}$C, $^{3}$H and $^{35}$S and other labels, target moieties and ligands.

Exemplary antineoplastic agents that find use for conjugating to the anti-DR4 antibodies include alkylating agents (e.g., nitrogen mustards, ethyleneimines and methylmelamines, methylhydrazine derivative, alkyl sulfonate, nitrosoureas, triazenes and platinum coordination complexes); antimetabolites (e.g., folic acid analogs, pyrimidine analogs, purine analogs; natural products (e.g., vinca alkaloids, taxanes, epipodophyllotoxins, camptothecins, antibiotics, and anthracenedione). In some embodiments, the anti-DR4 antibodies or antigen binding molecules are co-formulated with an antimetabolite antineoplastic agent, e.g., a folic acid analog (e.g., methotrexate, pemetrexed, trimetrexate), a pyrimidine analog (e.g., 5-fluorouracil, capecitabine, cytarabine, gemcitabine), a purine analog (e.g., mercaptopurine, pentostatin, cladribine fludarabine), or mixtures thereof. In some embodiments, the anti-DR4 antibodies or antigen binding molecules are co-formulated with an alkylating agent antineoplastic agent, e.g., nitrogen mustards (e.g., mechlorethamine, cyclophosphamide, ifosfamide, melphalan, chlorambucil), ethyleneimines (e.g., altretamine) and methylmelamines (e.g., thiotepa), methylhydrazine derivatives (e.g., procarbazine), alkyl sulfonate (e.g., busulfan), nitrosoureas (e.g., carmustine, streptozocin), triazenes (e.g., dacarbazine, temozolomide) and platinum coordination complexes (e.g., cisplatin, carboplatin, oxaliplatin). Additional antineoplastic drugs find use and are known in the art, and described, for example, in Chapter 51 of Brunton, et al., Goodman And Gilman's The Pharmacological Basis of Therapeutics, Eleventh Edition, 2006, McGraw-Hill and in Physicians' Desk Reference, $63^{rd}$ Edition, 2009, Thomson Reuters.

Exemplary cytotoxins include *Pseudomonas* exotoxins, Diphtheria toxins, ricin, and abrin. *Pseudomonas* exotoxin and Diphtheria toxin are most preferred. Suitable *Pseudomonas* exotoxin variants for use in delivery to tumor cells are well known in the art and described, for example, in U.S. Pat. Nos. 4,545,985; 5,458,878; 5,602,095; 5,705,163; 5,980,895; 6,074,644; 6,423,513; 6,426,075 and 6,518,061. In some embodiments, the effector moiety is *Pseudomonas* exotoxin, PE38.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

In a non-recombinant embodiment of the invention, effector molecules, e.g., therapeutic, diagnostic, or detection moieties, are linked to the anti-DR4 antibodies of the present invention using any number of means known to those of skill in the art. Both covalent and noncovalent attachment means may be used with anti-DR4 antibodies of the present invention.

The procedure for attaching an effector molecule to an antibody will vary according to the chemical structure of the EM. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules, such as those available from Pierce Chemical Company (Rockford Ill.).

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

4. Polynucleotides, Vectors and Host Cells for Producing Anti-DR4 Antibodies

The invention provides polynucleotides (DNA or RNA) which encode polypeptides comprising segments or domains of the anti-DR4 antibody chains or antigen-binding molecules described above. In some embodiments, the polynucleotides are substantially purified or isolated. Some of the polynucleotides of the invention comprise the polynucleotide sequence encoding a heavy chain variable region selected from the group consisting of SEQ ID NOs:37 and 39, and the polynucleotide sequence encoding a light chain variable region selected from the group consisting of SEQ ID NOs:36 and 38. Some other polynucleotides of the invention comprise nucleotide sequences that are substantially identical (e.g., at least 50%, 60%, 70%, 80%, 80%, 95%, 96%, 97%, 98% or 99%) to one of the nucleotide sequences shown in SEQ ID NOs:37-39. When expressed from appropriate expression vectors, polypeptides encoded by these polynucleotides are capable of exhibiting antigen binding capacity.

Also provided in the invention are polynucleotides which encode at least one CDR region and usually all three CDR regions from the heavy or light chain of the mouse anti-DR4 antibodies described in the Examples below. Some other polynucleotides encode all or substantially all of the variable region sequence of the heavy chain and/or the light chain of the mouse anti-DR4 antibodies. For example, some of these polynucleotides encode the amino acid sequence having at least about 50%, 60%, 70%, 80%, 90%, 93%, 95%, 96%, 97%, 98%, 99% or 100% sequence identity to the heavy chain variable region shown in SEQ ID NOs:37 or 39 and/or the amino acid sequence having at least about 50%, 60%, 70%, 80%, 90%, 93%, 95%, 96%, 97%, 98%, 99% or 100% sequence identity to the light chain variable region shown in SEQ ID NOs:36 or 38. Because of the degeneracy of the code, a variety of nucleic acid sequences will encode each of the immunoglobulin amino acid sequences.

The polynucleotides of the invention can encode only the variable region sequence of an anti-DR4 antibody. They can also encode both a variable region and a constant region of the antibody. Some of polynucleotide sequences of the invention nucleic acids encode a mature heavy chain variable region sequence that is substantially identical (e.g., at least 80%, 90%, or 99%) to the mature heavy chain variable region sequence shown in SEQ ID NO:2 or 4. Some other polynucleotide sequences encode a mature light chain variable region sequence that is substantially identical to the mature light chain variable region sequence shown in SEQ ID NO:1 or 3. Some of the polynucleotide sequences encode a polypeptide that comprises variable regions of both the heavy chain and the light chain of one of the exemplified mouse anti-DR4 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-DR4 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the anti-DR4 antibodies described above. Various expression vectors can be employed to express the polynucleotides encoding the anti-DR4 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the anti-DR4 polynucleotides and polypeptides in mammalian (e.g., human) cells include pThioHis A, B & C, pcDNA3.1/H is, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-DR4 antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-DR4 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-DR4 antibody sequences. More often, the inserted anti-DR4 antibody sequences are linked to a signal sequences before inclusion in the vector. Vectors to be used to receive sequences encoding anti-DR4 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-DR4 antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-DR4 polypeptides of the invention. Insect cells in combination with baculovirus vectors can also be used.

In some preferred embodiments, mammalian host cells are used to express and produce the anti-DR4 polypeptides of the present invention. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-DR4 antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

5. Methods of Inhibiting, Reducing and Preventing Cancers a. Conditions Subject to Treatment The agonistic anti-DR4 antibodies of the present invention find use in reducing, inhibiting or preventing the growth or progression of cancers or other hyperproliferative disorders mediated by cells that express or overexpress DR4.

In the context of effecting treatment, the patient has a cancer or a tumor burden, and administration of the anti-DR4 antibodies can reverse, delay or inhibit progression of the disease. In the context of effecting prevention, the patient may be in remission, or may have undergone the removal of a primary tumor, and administration of the anti-DR4 antibodies can reduce, inhibit or eliminate growth of metastasis. In some embodiments, antibodies of the invention that bind DR4 and stimulate apoptosis of DR4 expressing cells are used to treat, prevent or ameliorate cancer. In some embodiments, antibodies of the invention are used to inhibit the progression or metastasis of cancers and other related disorders.

Exemplary cancers that can be treated or prevented by administration of the anti-DR4 antibodies include, but are not limited to, colon cancer, cervical cancer, leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Burkitt's lymphoma, Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments, antibodies of the invention that bind DR4 and stimulate apoptosis of DR4 expressing cells are used to treat, prevent or ameliorate renal cancer.

In some embodiments, antibodies of the invention that bind DR4 and stimulate apoptosis of DR4 expressing cells are used to treat, prevent or ameliorate melanoma.

In some embodiments, antibodies of the invention that bind DR4 and stimulate apoptosis of DR4 expressing cells are used to treat, prevent or ameliorate cancers of the liver such as hepatomas.

In some embodiments, antibodies of the invention that bind DR4 and stimulate apoptosis of DR4 expressing cells are used to treat, prevent or ameliorate cancers of the central nervous system such as medulloblastioma, neuroblastoma, and glioblastoma.

It has been demonstrated, in accordance with the present invention that the expression of TRAIL receptor DR4 on lung carcinoma tissue, bladder carcinoma tissue and ovarian carcinoma tissue. Additionally, it has been demonstrated, in accordance with the present invention that TRAIL receptor DR4 is expressed on primary breast, colon, lung, and stomach tumor tissue. Thus, in highly preferred embodiments, antibodies of the invention that bind DR4 and stimulate apoptosis of DR4 expressing cells are used to treat lung cancer. In other highly preferred embodiments, antibodies of the invention that bind DR4 and stimulate apoptosis of DR4 expressing cells are used to treat bladder cancer. In other highly preferred embodiments, antibodies of the invention that bind DR4 and stimulate apoptosis of DR4 expressing cells are used to treat ovarian cancer. In other highly preferred embodiments, antibodies of the invention that bind DR4 and stimulate apoptosis of DR4 expressing cells are used to treat breast cancer. In other highly preferred embodiments, antibodies of the invention that bind DR4 and stimulate apoptosis of DR4 expressing cells are used to treat colon cancer and/or colorectal cancer. In other highly preferred embodiments, antibodies of the invention that bind DR4 and stimulate apoptosis of DR4 expressing cells are used to treat stomach cancer.

In some embodiments, antibodies of the invention that bind DR4 and stimulate apoptosis of DR4 expressing cells are used to treat, prevent or ameliorate renal cancer, melanoma, pancreatic cancer and cancers of the liver such as hepatomas.

In another embodiment, antibodies of the invention that bind DR4 and stimulate apoptosis of DR4 expressing cells are used to treat diseases and/or disorders associated with increased cell survival, or the inhibition of apoptosis, including cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, endothelioma, osteoblastoma, osteoclastoma, osteosarcoma, chondrosarcoma, adenoma, breast cancer, prostrate cancer, Kaposi's sarcoma and ovarian cancer); autoimmune disorders (such as multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. In preferred embodiments, the antibodies and antibody compositions of the invention are used to inhibit growth, progression, and/or metastasis of cancers, in particular those listed above. In preferred embodiments the antibodies and antibody compositions of the invention are not hepatotoxic, in vitro or in vivo.

b. Pharmaceutical Compositions and Administration

The antibody and/or immunoconjugate compositions of this invention are particularly useful for parenteral administration, for example intravenous, intraperitoneal, intrapleural, inhalational, intratumoral administration or administration into a body cavity or lumen of an organ. For example, ovarian malignancies may be treated by intravenous or intratumoral administration or by localized delivery (e.g., intraperitoneal) to the tissue surrounding the tumor. To treat cancers expressing DR4, pharmaceutical compositions of this invention comprising anti-DR4 antibodies or antibody fragments can be administered directly into the pleural or peritoneal cavities.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

The anti-DR4 antibodies can be administered in dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once daily, once weekly once a month or once every 3 to 6 months, as needed. Initial therapy regimes can involve more frequent administrations that are reduced upon observing a positive response to treatment in the patient. In some methods, two or more monoclonal antibodies with different binding specificities are administered simultaneously, in which case the dosage of each antibody administered falls within the ranges indicated. In some embodiments, antibodies or antibody fragments of the present invention can be co-administered with other anti-DR4 antibodies that bind to non-overlapping epitopes on DR4, e.g., antibodies described in U.S. Pat. Nos. 7,064,189; 7,252,994; and 7,476,383. Antibody is usually administered on multiple occasions.

Intervals between single dosages can be daily, weekly, monthly or yearly. Intervals can also be irregular as indicated by measuring blood levels of antibody to DR4 in the patient. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, e.g., applications during a remission, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

A typical pharmaceutical immunotoxin composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON: THE SCIENCE AND PRACTICE OF PHARMACY, 21ST ED., University of the Sciences in Philadelphia (USIP), Lippincott, Williams and Wilkins (2005). As noted in the Background, clinical trials of the anti-DR4 immunotoxin SS1P are underway, and dosage information from those trials can also be used to guide administration of immunotoxins using antibodies of the present invention. See, Hassan, et al., *Clin Cancer Res.* 2007 Sep. 1; 13(17):5144-9.

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Generally, lower doses are administered initially and incrementally increased until reaching a dose that is efficacious without causing undesirable side effects. Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has been shown to be an effective vehicle for formulation and sustained delivery of recombinant interleukin-2 and urease (Johnston, et al., *Pharm. Res.* 9:425-434 (1992); and Pee, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. One preferred application for the immunotoxins of the invention is the treatment of malignant cells expressing or overexpressing DR4. Exemplary malignant cells include solid cancers, including without limitation, lung cancer, renal cancer, cervical cancer, lymphomas (Burkitt's lymphoma), myelomas, and colorectal cancers.

c. Combination Therapies with Established Anticancer Therapies i. Chemotherapy

The anti-DR4 antibodies can be co-administered with other agents as combination therapies. In some embodiments the anti-DR4 antibodies may be co-administered with one or more chemotherapeutic agent.

Examples of chemotherapeutic agents that can be co-administered with the anti-DR4 antibodies include without limitation alkylating agents (cisplatin, carboplatin, and oxaliplatin); anti-metabolites (purine or pyrimidine mimetics including for example azathioprine and mercaptopurine); plant alkaloids and terpenoids (vinca alkaloids and taxanes); vinca alkaloids (vincristine, vinblastine, vinorelbine, and vindesine); podophyllotoxin (including etoposide and teniposide); taxanes (paclitaxel, taxol and docetaxel); topoisomerase inhibitors (Type I inhibitors: camptothecins, irinotecan and topotecan; Type II Inhibitors: amsacrine, etoposide, etoposide phosphate, and teniposide); antineoplastics (dactinomycin, doxorubicin, epirubicin, fludarabine and bleomycin). Any chemotherapeutic agent being used to treat the cancer of interest can be co-administered in a combination therapy regime with the anti-DR4 antibodies.

ii. Radiation

The anti-DR4 antibodies can be administered in conjunction with radiological procedures. A variety of radiological procedures are available for disease treatments. Any of the procedures know by one of skill can be combined with the polypeptides of the present invention for treatment of a patient. Radiological procedures comprise treatment using radiation therapy to damage cellular DNA. The damage to the cellular DNA can be caused by a photon, electron, proton, neutron, or ion beam directly or indirectly ionizing the atoms which make up the DNA chain. Indirect ionization occurs due to the ionization of water, forming free radicals, notably hydroxyl radicals, which then subsequently damage the DNA. In the most common forms of radiation therapy, the majority of the radiation effect is through free radicals. Due to cellular DNA repair mechanisms, using agents that induce double-strand DNA breaks, such as radiation therapies, has proven to be a very effective technique for cancer therapy. Cancer cells are often undifferentiated and stem cell-like, such cells reproduce more rapidly and have a diminished ability to repair sub-lethal damage compared healthy and more differentiated cells. Further, DNA damage is inherited through cell division, leading to an accumulation of damage to the cancer cells, inducing slower reproduction and often death.

The amount of radiation used in radiation therapy procedure is measured in gray (Gy), and varies depending on the type and stage of cancer being treated and the general state of the patient's health. The dosage range can also be affected by cancer type, for example, the typical curative dosage for a solid epithelial tumor ranges from 60 to 80 Gy, while the dosage for lymphoma ranges from 20 to 40 Gy.

Preventative (adjuvant) doses can also be employed and typically range from 45 to 60 Gy administered in 1.8 to 2 Gy fractions (for breast, head and neck cancers). Many other factors are well-known and would be considered by those of skill when selecting a dose, including whether the patient is receiving other therapies (such as for example, but not limited to administration of the anti-DR4 antibodies, administration of chemotherapies and the like), patient co-morbidities, timing of radiation therapy (for example, whether radiation therapy is being administered before or after surgery), and the degree of success of any surgical procedures.

Delivery parameters of a prescribed radiation dose can be determined during treatment planning by one of skill. Treatment planning can be performed on dedicated computers using specialized treatment planning software. Depending on the radiation delivery method, several angles or sources may be used to sum to the total necessary dose. Generally, a plan is devised that delivers a uniform prescription dose to the tumor and minimizes the dosage to surrounding healthy tissues.

iii. Surgery

The anti-DR4 antibodies can be administered in conjunction with surgical removal or debulking of tumors. A variety of surgical procedures are available for disease treatments. Any of the procedures know by one of skill can be combined with the polypeptides of the present invention for treatment of a patient. Surgical procedures are the commonly categorized by urgency, type of procedure, body system involved, degree of invasiveness, and special instrumentation.

Examples of surgical procedure can include emergency as well as scheduled procedures. Emergency surgery is surgery that must be done quickly to save life, limb, or functional capacity. Further examples of surgical procedures can include exploratory surgery, therapeutic surgery amputation, replantation, reconstructive, cosmetic, excision, transplantation or removal of an organ or body part, as well as others know in the art. Exploratory surgery can be performed to aid or confirm a diagnosis. Therapeutic surgery treats a previously diagnosed condition. Amputation involves cutting off a body part, usually a limb or digit. Replantation involves reattaching a severed body part. Reconstructive surgery involves reconstruction of an injured, mutilated, or deformed part of the body. Cosmetic surgery can done to improve the appearance of an otherwise normal structure or for repair of a structure damaged or lost due to disease. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

In addition to traditional open surgical procedure that employ large incisions to access the area of interest, surgery procedures further include minimally invasive surgery. Minimally invasive surgery typically involves smaller outer incision(s) which are employed for insertion of miniaturized instruments within a body cavity or structure, as in laparoscopic surgery or angioplasty. Laser surgery involves the use of a laser for cutting tissue instead of a scalpel or similar surgical instruments. Microsurgery involves the use of an operating microscope for the surgeon to see small structures. Robotic surgery makes use of a surgical robot (such as for example the Da Vinci (Intuit Surgical, Sunnyvale, Calif.)), to control the instrumentation under the direction of one of skill, such as for example a surgeon.

d. Methods of Monitoring Efficacy

A variety of methods can be employed in determining efficacy of therapeutic and prophylactic treatment with the anti-DR4 antibodies of the present invention. Generally, efficacy is the capacity to produce an effect without significant toxicity. Efficacy indicates that the therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. The anti-DR4 antibodies can be screened for prophylactic or therapeutic efficacy in animal models in comparison with untreated or placebo controls. The anti-DR4 antibodies identified by such screens can be then analyzed for the capacity to induce tumor cell death. For example, multiple dilutions of sera can be tested on tumor cell lines in culture and standard methods for examining cell death or inhibition of cellular growth can be employed. (See, e.g., Maniatis, et al., *Molecular Cloning: A Laboratory Manual*, Cold Spring Harbor Lab., New York, 1982; Ausubel, at al. Editor, *Current Protocols in Molecular Biology*, USA, 1984-2008; and Ausubel, et al. Editor, *Current Protocols in Molecular Biology*, USA, 1984-2008; Bonifacino, et al., Editor, *Current Protocols in Cell Biology*, USA, 2010; all of which are incorporated herein by reference in their entirety.)

The methods of the present invention provide for detecting inhibition disease in patient suffering from or susceptible to various cancers. A variety of methods can be used to monitor both therapeutic treatment for symptomatic patients and prophylactic treatment for asymptomatic patients.

Monitoring methods entail determining a baseline value of a tumor burden in a patient before administering a dosage of anti-DR4 antibodies, and comparing this with a value for the tumor burden after treatment, respectively.

With respect to therapies using the anti-DR4 antibodies, a significant decrease (i.e., greater than the typical margin of experimental error in repeat measurements of the same sample, expressed as one standard deviation from the mean of such measurements) in value of the tumor burden signals a positive treatment outcome (i.e., that administration of the anti-DR4 antibodies has blocked or inhibited, or reduced progression of tumor growth and/or metastasis).

In other methods, a control value of tumor burden (e.g., a mean and standard deviation) is determined from a control population of individuals who have undergone treatment with the anti-DR4 antibodies. Measured values of tumor burden in a patient are compared with the control value. If the measured level in a patient is not significantly different (e.g., more than one standard deviation) from the control value, treatment can be discontinued. If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant decrease in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can be analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

e. Kits

In another embodiment, this invention provides for kits for the detection of DR4 or an immunoreactive fragment thereof, (i.e., collectively, a "DR4 protein") in a biological sample. A "biological sample" as used herein is a sample of biological tissue or fluid that contains DR4. Such samples include, but are not limited to, tissue from biopsy, sputum, amniotic fluid, blood, and blood cells (e.g., white cells). Biological samples also include sections of tissues, such as frozen sections taken for histological purposes. A biological sample is typically obtained from a multicellular eukaryote, preferably a mammal such as rat, mouse, cow, dog, guinea pig, or rabbit, more preferably from a primate, such as a macaque, chimpanzee, and most preferably from a human.

In other embodiments, the kits contain an anti-DR4 antibody formulated for therapeutic purposes.

Kits will typically comprise an anti-DR4 antibody or antibody fragment of the present invention, the embodiments being as described herein. In some embodiments, the anti-DR4 antibody or antibody fragment will be an anti-DR4Fv fragment, such as a scFv fragment.

In addition the kits will typically include instructional materials disclosing means of use of an antibody of the present invention (e.g. for detection of DR4 expressing target cells in a sample, or for the reduction, inhibition or prevention of growth or progression of cancers expressing DR4).

For therapeutic purposes, the kits may also include one or more agents for co-administration with the anti-DR4 antibodies of the invention. For example, the kits, may also contain a second anti-DR4 antibody that binds to a non-overlapping or non-competing epitope on DR4. In other embodiments, the kits further contain an anti-DR5 antibody. In some embodiments, the kits contain one or more antineoplastic agents.

For diagnostic purposes, the kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting DR4 in a biological sample generally comprises the steps of contacting the biological sample with an antibody which specifically reacts, under immunologically reactive conditions, to DR4. The antibody is allowed to bind to DR4 under immunologically reactive conditions, and the presence of the bound antibody is detected directly or indirectly. The anti-DR4 antibody may be used, for example, as the capture antibody of an ELISA, or as a second antibody to bind to DR4 captured by the capture antibody. In some embodiments, the kits comprise an antibody or antibody fragment pre-bound to a solid support, e.g., a microchip, a microtiter plate or a bead. As is known in the art, the presence of the second antibody is typically then detected.

The antibodies provided herein are useful as diagnostic agents and in in vitro assays to detect the presence of DR4 in biological samples. For example, the antibodies m921 and m922 and variants of these antibodies as described herein can be used as the targeting moieties of immunoconjugates in immunohistochemical assays to determine whether a sample contains cells expressing DR4. If the sample is one taken from a tissue of a patient which should not normally express DR4, detection of DR4 would indicate either that the patient has a cancer characterized by the presence of DR4-expressing cells, or that a treatment for such a cancer has not yet been successful at eradicating the cancer.

In another set of uses for the invention, immunotoxins targeted by antibodies of the invention can be used to purge targeted cells from a population of cells in a culture. Thus, for example, cells cultured from a patient having a cancer expressing DR4 can be purged of cancer cells by contacting the culture with immunotoxins which use an m921 antibody or an m922 antibody (such as a Fab or scFvs) as a targeting moiety.

Although the present invention has been described in some detail by way of illustration and example for purposes of clarity of understanding, it will be obvious that certain changes and modifications may be practiced within the scope of the appended claims.

EXAMPLES

The following examples are offered to illustrate, but not to limit the claimed invention.

Example 1

Materials and Methods

Materials Recombinant human rTRAIL receptor 1 (DR4) that included the cysteine-rich and TNF receptor-like portions of the extracellular domain was purchased from Peprotech Inc. A mouse DR4-specific monoclonal antibody was purchased from Santa Cruz Biotechnology. ST486 Burkitt's human B cell lymphoma cell line was purchased from ATCC.

Screening of Human Naïve Fab Phage Displayed Library

The Fab library displayed on phage was constructed as previously described[19] and panned and screened with DR4 according to the method described by Feng et al.[20] Briefly, DR4 was coated in Maxisorp plate overnight at 4° C., and blocked with filtered 2% non-fat dry milk in phosphate buffered saline (MPBS). For each round of panning approximately $1\times10^{12}$ pfu phages were used. After incubation of phage on plate for 2 hours, the plate was washed with PBST (PBS+0.05% Tween 20) to remove non-binding phages. Exponentially growing E. coli TG1 culture was added to wells to allow remaining phages to infect the bacterial cells. After 30 min incubation of TG1 with phages, the culture was recovered and spread on bioassay dishes. Ninety-six colonies from 4th and 5th round panning were picked and screened for binding to DR4. Among them, twenty positive clones were selected and sequenced. Fifteen (75%) of these clones (named m921) were identical to each other; 5 (25%) of the clones (named m922) had a different sequence, but were identical to each other. These two clones were further characterized.

Recombinant Fab was prepared by transforming HB2151 E. coli with the plasmid carrying the Fab sequence, and expression was induced with 1 mM IPTG. Soluble Fab protein was released from the periplasm with polymyxin B treatment and Fab was purified using a Ni-chelating column, followed by the gel filtration on Superdex 75 10/300 GL column.

Converting Fabs into IgGs. The VH and VL+CL of clone m921 and m922 were sequentially subcloned into IgG expression vector pDR12.[21] For production of IgG, 293 Free Style cells were transfected with pDR12-IgG m921 or pDR12-IgG m922 with polyethylenimine. IgG was purified from 5 day conditioned medium with protein G column. The final preparation was dialyzed in PBS and filtered. Stable CHO expression clones were made later to produce larger quantity of IgG m921 and m922 in serum free medium.

Competition ELISA with rTRAIL To testing binding of recombinant antibodies to DR4 in vitro, DR4 protein was coated onto half-area ELISA plate at 50 ng/well. After blocking with MPBS, different dilutions of antibodies were incubated with coated wells. For detection of binding antibodies, secondary antibody goat anti-Flag tag-HRP and goat anti-human Fc-HRP (both used at 1:1000) were used to detect Fab or IgG. The ELISA signal was developed with substrate ABTS, and read under wavelength 405 nm. To test whether the antibodies compete with rTRAIL or other antibodies for binding with DR4, IgG m921 and m922 at 10 nM was pre-incubated with various concentrations of rTRAIL or other antibodies at room temperature for 30 min. The mixture was then added to wells for ELISA. Binding of IgG was in the presence of rTRAIL or competing antibody was detected.

FACS ST486 cells were rinsed in PBS and resuspended in the growth medium at 1 million/ml. DR4 mouse mAb (Santa Cruz Biotechnology) and DR41gG m921 or m922 was incubated with ST486 cells at 24 nM for 1 hour on ice. Cells were rinsed with growth medium twice and incubated with goat anti-mouse IgG-FITC or goat anti-human IgG-FITC at 1:1000. After 30 minute incubation cells were washed and resuspended in PBS.

Growth inhibition in ST486 Cells ST486 cells were seeded in 96-well plates at 3000 cells/well in growth medium. Six hours later, treatment medium made with various concentrations of m921 and m922 IgG in serum free RPMI was added to corresponding wells at 50 μl/well. Each treatment was repeated in six replicates. The plates were then incubated at 37° C. Two days later, 100 μl CellTiter-Glo Luminescent Cell Viability Assay reagent was added to each sample well. The reagent detects the ATP levels, which is present in live cells. Cells were incubated with the reagent at room temperature on an orbital shaker for 10 min. An equal aliquot of the reaction mixtures was transferred to a clean all-white 96-well plate for reading of luminescent signals.

Results:

Identification of DR4-specific Human mAb from a Naïve HUMAN FAB LIBRARY

Figure 1B:
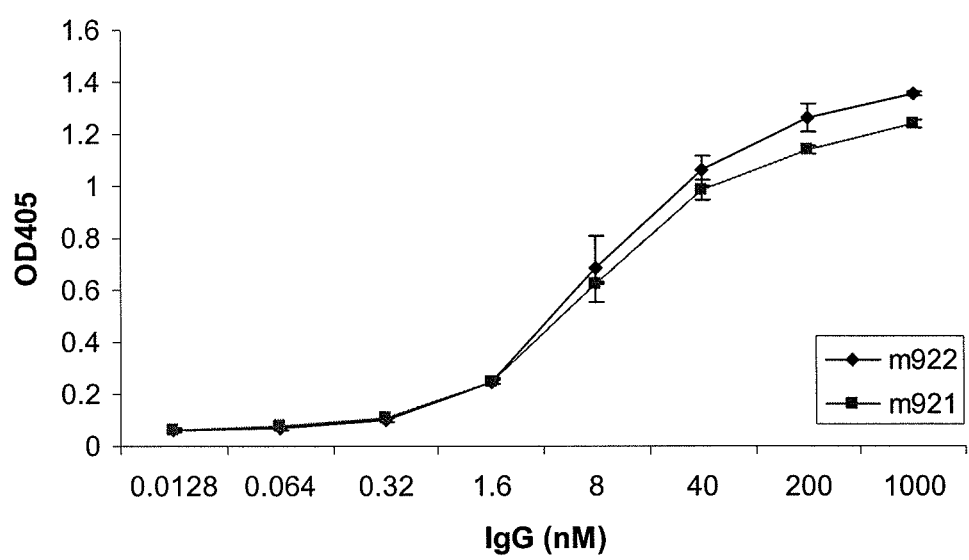

A human naïve phage displayed Fab library[19] was panned against a recombinant DR4 that included most of the extracellular domain (amino acids 25-239 based on sequence in NCBI accession NP-003835) of DR4 (FIG. 1A). Two clones, m921 and m922, were selected based on their high level of binding to DR4. The two clones belong to the same subtypes of light chain and heavy chain genes, and share 90% and 94% of identity in their light and heavy chain amino acid sequences, respectively. Compared to their corresponding germline V genes, they have high identities (99.3%-100%), with the exception of the V gene of m921 light chain which had 92% identity. Fabs were converted to IgG1s. The ELISA binding profile of the two IgG1s is presented in FIG. 1B. The antibodies bound with similar high-avidity (EC50~10 nM) to DR4, but did not bind to DR5 even at the highest (1000 nM) concentration tested (data not shown). To produce sufficient amount of IgG1s for subsequent tests, stable clones of Chinese hamster ovary (CHO) cells carrying the expression vector were generated and the antibodies were purified from serum-free conditioned medium.

M921 and m922 Competed with the DR4 Ligand rTRAIL

Figure 2A:
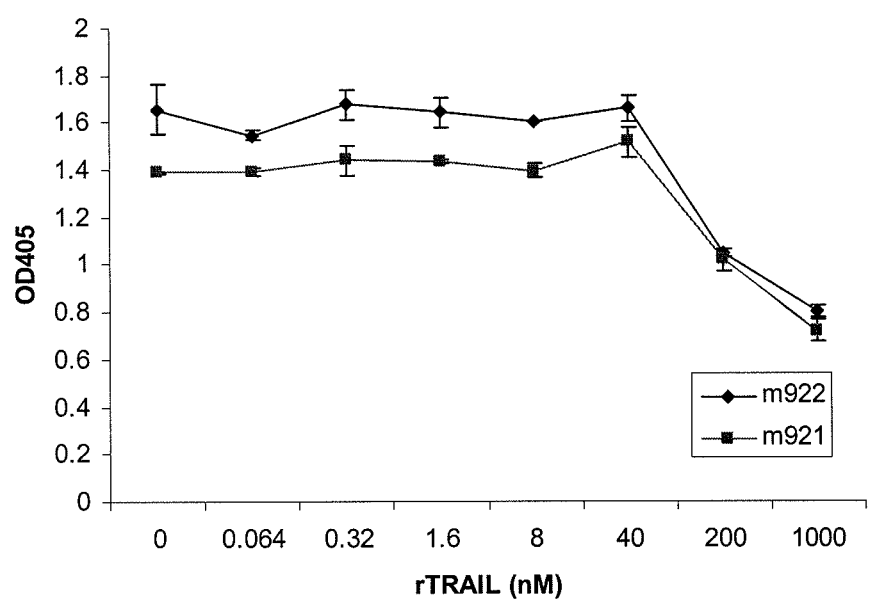
FIG. 2. Competition of m921 and m922 with rTRAIL and other antibodies for DR4 binding in vitro. A, DR4 was first coated on ELISA plate, m921 (-■-) or m922 IgG (-♦-), at 10 nM was pre-incubated with various concentrations of soluble recombinant TRAIL (rTRAIL), before they were added to ELISA wells. Binding of IgG was detected and plotted against different concentrations of competing rTRAIL. B, m921 or m922 IgG was incubated with various concentrations of competing mouse/rabbit IgG, before they were added to ELISA wells with DR4 protein coated. Binding of m921 or m922 was detected. C, Each competing antibody was tested separately at concentrations from 0.8 nM to 100 nM to confirm their binding to DR4.
Figure 2B:
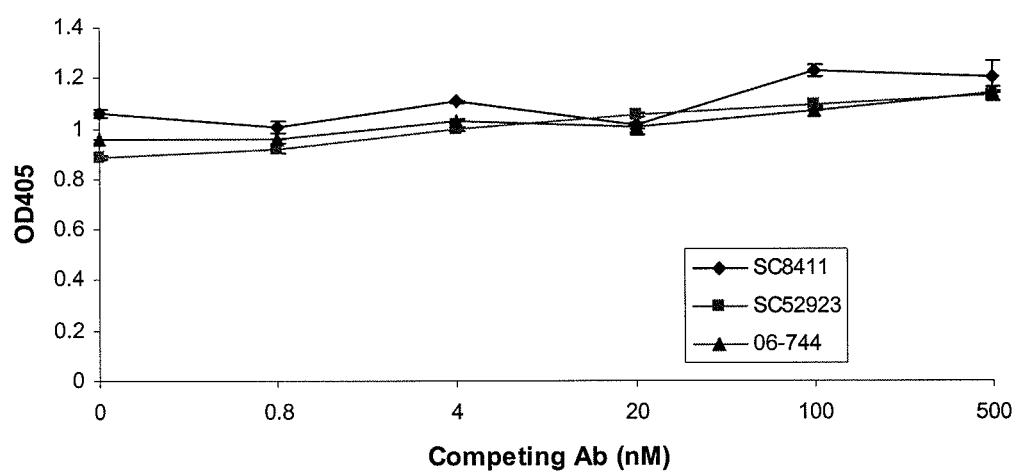
Figure 2C:
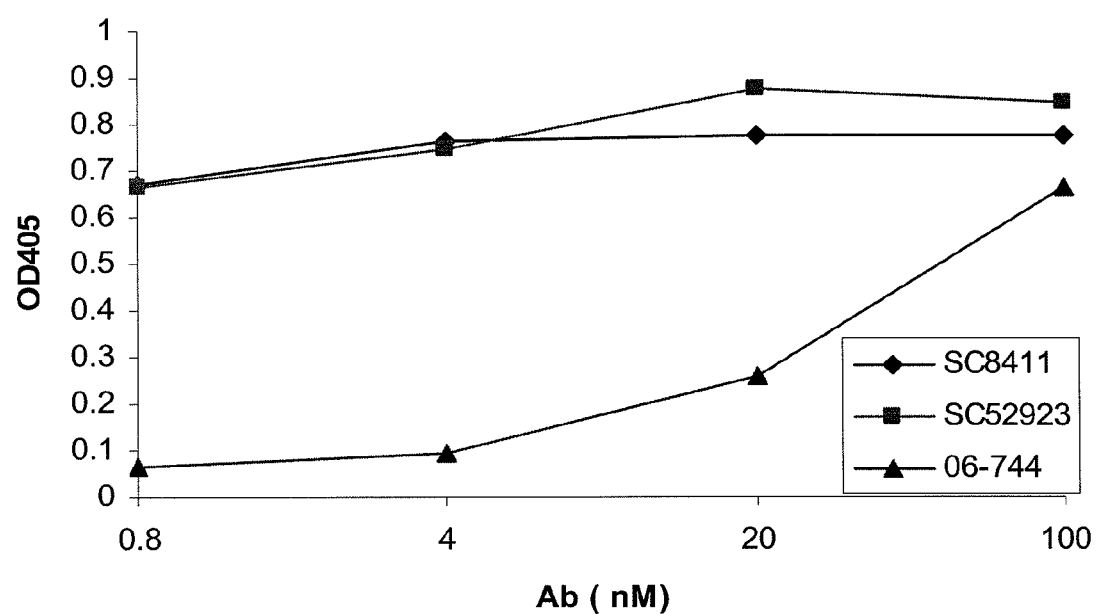

Death receptors DR4 and DR5 are activated by binding of the homotrimeric ligand TRAIL, through which the receptors are also trimerized. To determine whether the two newly identified antibodies bound to epitopes overlapping the rTRAIL binding site, DR4 was coated on an ELISA plate and prepared antibody solution at 10 nM mixed with various concentrations of recombinant TRAIL (rTRAIL). After incubation at room temperature for 30 min, the mixtures were added to ELISA wells. At TRAIL concentrations below 40 nM, the binding of the two IgG1s was not diminished (FIG. 2). The presence of rTRAIL decreased their binding to DR4 only at TRAIL concentrations higher than 40 nM (200 and 1000 nM). These results indicate that the binding sites of m921 and m922 are not identical to the binding site of rTRAIL, but could partially overlap with the binding site of rTRAIL on DR4.

To further map the epitopes of m921 and m922, three commercially available mouse/rabbit antibodies that bind specifically to known epitopes of human DR4 were obtained. SC8411 was raised against amino acid 1-130 of human DR4, and its epitope is thought to be close to the N-terminus of DR4. SC52923 and the rabbit polyclonal Ab 06-744 have their epitopes at amino acids 1-20 and 77-90, respectively. All three antibodies bind with high affinity to DR4 on ELISA at the concentrations tested (0.8 to 100 nM). During competition ELISA, the concentrations of m921 and m922 were kept constant at 10 nM, while the concentrations of the competition antibodies were varied from 0.8 to 500 nM. Results showed that the two mouse mAbs and the rabbit polyclonal antibodies did not compete with m921 or m922. Since m921 and m922 were screened with recombinant human DR4 extracellular domain with amino acid 25-239, it is understandable that SC52923 did not compete with either antibody. Anti-DR4 antibodies currently in clinical studies were not obtained. Therefore, determination of how the epitopes of the present anti-DR4 antibodies related to those of the clinical candidates was not made.

Binding of m921 and m922 to Cell Surface-associated DR4

Figure 3:
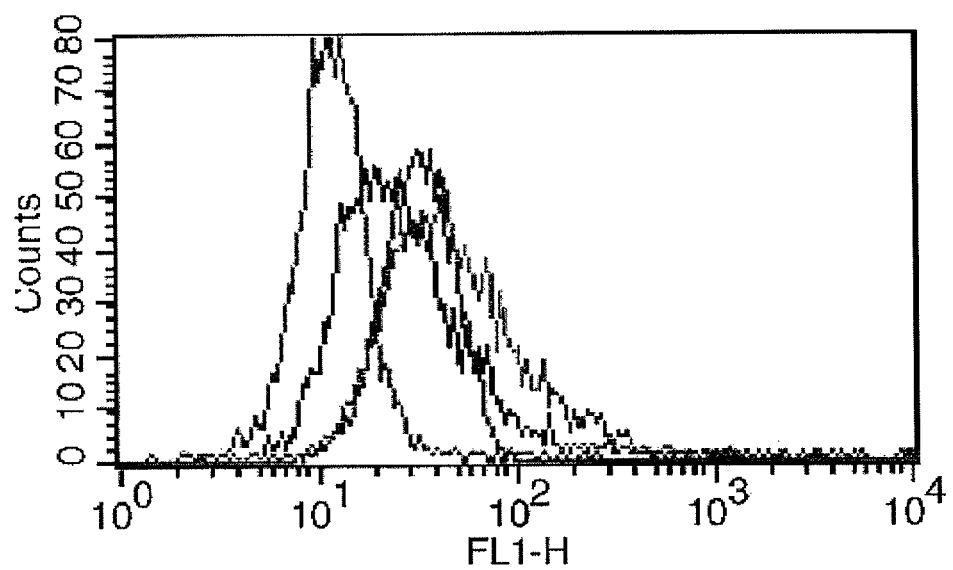
FIG. 3. Flow cytometry of DR4 binding to m921 and m922 on ST486 cells. ST486 cells were incubated with 24 nM primary antibodies for 1 hour on ice, followed by 2 ul of corresponding FITC-conjugated secondary antibodies for 30 minutes. Black line, a control human monoclonal Ab. Green line, DR4 mouse monoclonal antibody from Santa Cruz Biotechnology. Red line, DR4 IgG m921. Blue line, DR4 m922 IgG.

Binding of the antibodies to cell surface-associated native DR4 was tested by using the Burkitt's B cell lymphoma cell line ST486, which expresses DR4 and is sensitive to DR4-targeting antibodies.[13] These cells have moderate levels of DR4 as measured by a mouse mAb that was used as a positive control (FIG. 3). Compared to the mouse mAb, m921 binding yielded a similar shift on the flow cytometry profile at the same concentration. In contrast, m922 did not show binding to cell surface-associated DR4, despite its similar binding to DR4 on ELISA, which suggests that there are differences in their epitopes. Alternatively, cell surface DR4 may have a slightly different conformation compared with DR4 coated on the ELISA plate that could account for the difference in binding, i.e., the cell surface DR4 may maintain the m921, but not the m922 epitope.

M921 Inhibits ST486 Cell Growth

Figure 4:
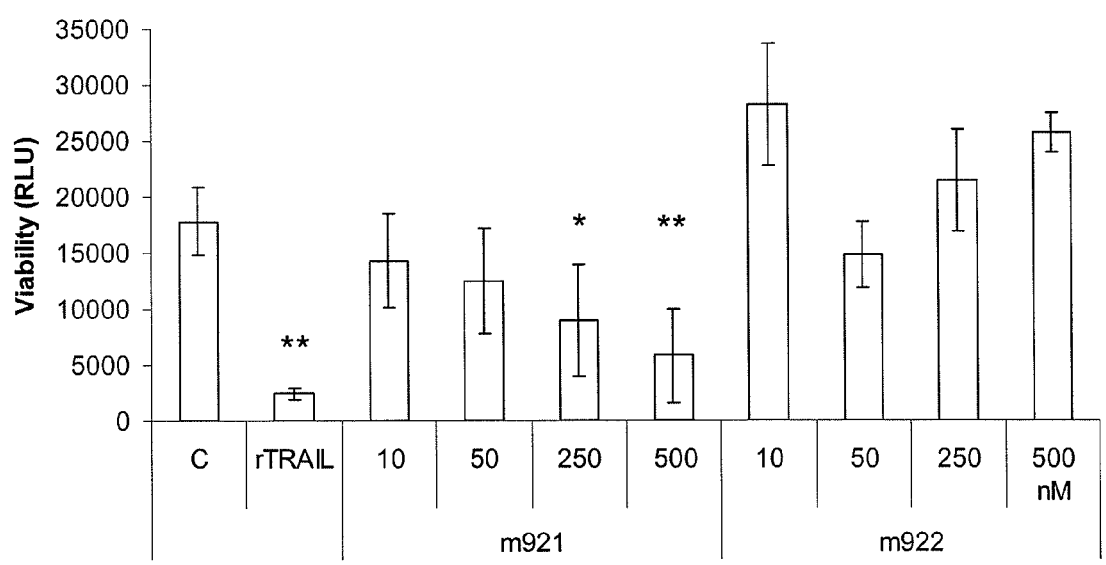
FIG. 4. Growth of ST486 in the presence of DR4 m921 and m922. ST486 cells were seeded in clear 96-well culture plates at 3000 cells/well. Treatment media with antibodies were added to wells. m921 or m922 IgG concentrations are at 10, 50, 250, or 500 nM in the final culture samples. Cells were treated with 5 nM of soluble recombinant TRAIL (rTRAIL) as positive control. An isotype control IgG at 500 nM was included as negative control (C). Cell viability was monitored 48 hours after the treatment. Six wells were set up for each treatment. The graph shown here is a representative result. Readings from each treatment were compared with those from the control group in a t-Test analysis, * in graph stands for $p<0.05$, and ** stands for $p<0.01$.

To determine whether the DR4 antibodies can inhibit cancer cell growth, ST486 Burkitt's lymphoma human cells were used. The cells were set up in complete growth medium, and then treated with medium plus various concentrations of m921 and m922. Recombinant TRAIL (rTRAIL) was used as positive control. As expected, ST486 cells were susceptible to rTRAIL treatment. At 5 nM concentration, there were only a few viable cells in the rTRAIL-treated sample, compared with the isotype control IgG treatment. M921 IgG showed inhibition of growth in a dose-dependent manner (FIG. 4), whereas m922 IgG had no effect on cell growth. These results are consistent with the flow cytometry results for the two IgGs (FIG. 3). In cells where the DR4 surface expression level is below the detection limit (e.g., MCF-7 cells), m921 treatment did not change growth profiles within the duration of the experiment (data not shown), indicating that growth inhibition of ST486 cells by m921 is pathway specific, rather than non-specific cellular toxicity.

Discussion

Two DR4-specific human mAbs, m921 and m922, have been identified that bind with relatively high avidity (nM range) to rDR4, but only m921 bound to cell surface-associated native DR4 and inhibited cancer cell growth. There are at least two possible explanations: 1) rDR4 exhibits a binding site (or portions of the binding site) that is not exposed on the native cell surface-associated DR4; and 2) portions of rDR4 were exposed due to conformational changes resulting from the absence of the DR4 transmembrane and surrounding regions.

M921 exhibits agonistic functions, which is indicative that its binding site overlaps the TRAIL binding site. It is known that binding of TRAIL to DR5 involves two separate patches of the receptor; presumably the same is true of DR4.[3] The two patches span a wide range of the ectodomain of DR4/DR5; therefore, a recombinant DR4 that included most of the extracellular part of DR4 was used for immunization and screening. M921 could bind to both patches or induce an agonistic response by a different mechanism. The agonistic antibodies may have subtle differences in their epitopes that could be important in inducing apoptosis effectively.

Since rTRAIL binds to both DR4 and DR5, there may be an advantage to using rTRAIL to activate this pathway;[4] however, specific activation of DR4, but not DR5, may be needed under some conditions, and therefore an agonistic anti-DR4 antibody such as m921 could be useful. It is known that the levels of DR4 and DR5 expression on cell surfaces do not directly correlate with susceptibility to TRAIL pathway therapeutics. This antibody could be used as a research reagent to delineate the contribution of DR4 and DR5, respectively, to apoptosis in various cells. On ST486 cells, the binding of m921 to DR4 showed comparable results to those of a mouse mAb. M921 inhibited the growth of these cells without affecting DR4-negative cells, e.g., MCF-7, which suggests that m921 finds use as a candidate antibody for an anti-cancer therapeutic targeting the TRAIL pathway.

REFERENCES

1. Ashkenazi, A. Nat Rev Drug Disc 7:1001-12 2008
2. Smith, C. A. et al., Cell 76:959-62 1994
3. Hymowitz, S. G. et al., Mole Cell 4:563-71 1999
4. Ashkenazi, A. et al., J Clin Invest 118:1979-90 2008
5. Kaufmann, S. H. et al., Oncogene 22:7414-30 2003
6. Shankar, S. et al., Int J Oncol 24:1133-40 2004
7. Jin, H. et al., Cancer Res 64:4900-5 2004
8. Muhlethaler-Mottet, A. et al., Oncogene 23:5415-25 2004
9. Pollack, I. F. et al., Clin Cancer Res 7:1362-9 2001
10. Sayers, T. J. et al., Cancer Immunol Immunother 55:76-84 2006
11. Jo, M. et al., Nat Med 6:564-7 2000
12. Yoshida, T. et al., Mol Cancer Res 7:1835-44 2009
13. Pukac, L. et al., Br J Cancer 92:1430-41 2005
14. Griffith, T. S. et al., J Immunol 162:2597-605 1999
15. Ichikawa, K. et al., Nat Med 7:954-60 2001
16. Adams, C. et al., Cell Death Differ 15:751-61 2008
17. Leong, S. et al., J Clin Oncol 27:4413-21 2009
18. Frew, A. J. et al., Proc Natl Acad Sci USA 105:11317-22 2008
19. Zhu, Z. et al., Methods Mol Biol 525:129-42, xv 2009
20. Feng, Y. et al., Mol Cancer Ther 5:114-20 2006
21. Burton, D. R. et al., Science 266:1024-7 1994

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCES

SEQ ID NO: 1

- M921 Light chain variable region: CDR1, CDR2, CDR3 underlined

QPVLTQPPSASATPGQRVTISCSGS<u>SSNIGSNT</u>LDWFQQLPGTAPKLLIF<u>DTNRRPSGVPDR</u>

FSGSKSGTSASLAISGLQAEDEAVYFC<u>ATWDNSLNGAV</u>FGGGTKLSVPRQAKAAPSVTLFPP

SSEELQANKATLVCLISDFYPGAVTVAWKADSSPVKAGVETTTPSKQSNNKYAASSYLSLTP

EQWKSHRSYSCQVTHEGSTVEKTVAPTECS

SEQ ID NO: 2

- M921 Heavy chain variable region: CDR1, CDR2, CDR3 underlined

QVQLQQSGPGLVKPSQTLSLTCAIS<u>GDSVSSNSAA</u>WNWIRQSPSRGLEWLGR<u>TYYRSKWYND</u>

YAVSVKGRITINPDTSKNQFSLQLNSVTPEDTAVYYC<u>ARDLGVAAADSYYYYGMDV</u>WGQGTT

```
                                                          -continued
VTVSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVGPKSCDKTSGQAG

SEQ ID NO: 3
- M922 Light chain variable region: CDR1, CDR2,
CDR3 underlined
QSVLTQPPSASGTPGQRVTISCSGSSSNIGSNTVNWYQQLPGTAPKLLIYSNNQRPSGVPDR

FSGSKSGTSASLAISGLQSEDEADYYCAAWDDSLNGRVVFGGGTKLTVLGQPKAAPSVTLFP

PSSEELQANKATLVCLISDFYPGAVTVAWKADSSPVKAGVETTTPSKQSNNKYAASSYLSLT

PEQWKSHKSYSCQVTHEGSTVEKTVAPTECS

SEQ ID NO: 4
- M922 Heavy chain variable region: CDR1, CDR2,
CDR3 underlined
QVQLQQSGPGLVKPSQTLSLTCAISGDSVSSNSAAWNWIRQSPSRGLEWLGRTYYRSKWYND

YAVSVKSRITINPDTSKNQFSLQLNSVTPEDTAVYYCARETVAVDAFDIWGQGTMVTVSSAS

TKGPSVFPLAPSSKSTSGGTAALGCLVKDYFPEPVTVSWNSGALTSGVHTFPAVLQSSGLYS

LSSVVTVPSSSLGTQTYICSVNHKPSNTKVDKKVEPKSCDKTSGQAG

SEQ ID NO: 5
- M921 and M922 light chain CDR1
SSNIGSNT

SEQ ID NO: 6
- M921 light chain CDR2
DTN

SEQ ID NO: 7
- M921 light chain CDR3
ATWDNSLNGAVF

SEQ ID NO: 8
- M921 and M922 heavy chain CDR1
GDSVSSNSAA

SEQ ID NO: 9
- M921 and M922 heavy chain CDR2
TYYRSKWYN

SEQ ID NO: 10
- M921 heavy chain CDR3
ARDLGVAAADSYYYYGMDVW

SEQ ID NO: 11
- M922 light chain CDR2
SNN

SEQ ID NO: 12
- M922 light chain CDR3
AAWDDSLNGRVVF

SEQ ID NO: 13
- M922 heavy chain CDR3
ARETVAVDAFDIW

SEQ ID NO: 14
- M921 light chain FR1
QPVLTQPPSASATPGQRVTISCSGS

SEQ ID NO: 15
- M921 light chain FR2
LDWFQQLPGTAPKLLIF

SEQ ID NO: 16
- M921 light chain FR3
RRPSGVPDRFSGSKSGTSASLAISGLQAEDEAVYFC

SEQ ID NO: 17
- M921 light chain FR4
GGGTKLSVPR
```

-continued

- M921 and M922 heavy chain FR1  
QVQLQQSGPGLVKPSQTLSLTCAIS  
SEQ ID NO: 18

- M921 and M922 heavy chain FR2  
WNWIRQSPSRGLEWLGR  
SEQ ID NO: 19

- M921 heavy chain FR3  
DYAVSVKGRITINPDTSKNQFSLQLNSVTPEDTAVYYC  
SEQ ID NO: 20

- M921 heavy chain FR4  
GQGTTVTVSSA  
SEQ ID NO: 21

- M922 light chain FR1  
QSVLTQPPSASGTPGQRVTISCSGS  
SEQ ID NO: 22

- M922 light chain FR2  
VNWYQQLPGTAPKLLIY  
SEQ ID NO: 23

- M922 light chain FR3  
QRPSGVPDRFSGSKSGTSASLAISGLQSEDEADYYC  
SEQ ID NO: 24

- M922 light chain FR4  
FGGGTKLTVLG  
SEQ ID NO: 25

- M922 heavy chain FR3  
DYAVSVKSRITINPDTSKNQFSLQLNSVTPEDTAVYYC  
SEQ ID NO: 26

- M922 heavy chain FR4  
GQGTMVTVSSA  
SEQ ID NO: 27

- light chain FR2 consensus  
(L/V)(D/N)WFQQLPGTAPKLLI(F/Y)  
SEQ ID NO: 28

- light chain FR3 consensus  
(R/Q)RPSGVPDRFSGSKSGTSASLAISGLQ(A/S)EDEA(V/D)Y(F/Y)C  
SEQ ID NO: 29

- heavy chain FR3 consensus  
DYAVSVK(S/G)RITINPDTSKNQFSLQLNSVTPEDTAVYYC  
SEQ ID NO: 30

-light chain CDR2 consensus  
(D/S)(N/T)N  
SEQ ID NO: 31

-light chain CDR3 consensus  
A(A/T)WD(D/N)SLNG(A/R)V(V/X)F, wherein X = no amino acid  
SEQ ID NO: 32

- light chain variable segment (FR1-CDR1-FR2-CDR2-FR3) consensus

Q(P/S)VLTQPPSAS(A/G)TPGQRVTISCSGSSSNIGSNT(L/V)DWFQQLPGTAPKLLI (F/Y)(D/S)(S/T)N(R/Q)RPSGVPDRFSGSKSGTSASLAISGLQ(A/S)EDEA(D/V)Y (F/Y)C  
SEQ ID NO: 33

- heavy chain variable segment (FR1-CDR1-FR2-CDR2-FR3) consensus

QVQLQQSGPGLVKPSQTLSLTCAISGDSVSSNSAAWNWIRQSPSRGLEWLGRTYYRSKWYND

YAVSVK(S/G)RITINPDTSKNQFSLQLNSVTPEDTAVYYC  
SEQ ID NO: 34

SEQ ID NO: 35

- DR4 (TNFRSF10A tumor necrosis factor receptor
superfamily, member 10a)
GenBank Accession No. NM_003844.3 → NP_003835.3
  1 mappparvhl gaflavtpnp gsaasgteaa aatpskvwgs sagrieprgg
grgalptsmg 61 qhgpsarara grapgprpar easprlrvhk tfkfvvvgvl lqvvpssaat
iklhdqsigt 121 qqwehsplge lcppgshrse hpgacnrcte gvgytnasnn lfaclpctac
ksdeeerspc 181 tttrntacqc kpgtfrndns aemcrkcsrg cprgmvkvkd ctpwsdiecv
hkesgnghni 241 wvilvvtlvv plllvavliv cccigsgcgg dpkcmdrvcf wrlgllrgpg
aednahneil 301 snadslstfv seqqmesqep adltgvtvqs pgeaqcllgp aeaegsqrrr
llvpangadp 361 tetlmlffdk fanivpfdsw dqlmrqldlt kneidvvrag tagpgdalya
mlmkwvnktg 421 rnasihtlld alermeerha rekiqdllvd sgkfiyledg tgsavsle

SEQ ID NO: 36

- m921 light chain nucleic acid sequence
cagcctgtgctgactcagccacc ctcagcgtctgcgaccccggacagagggtcaccatctcttgctctggaagcagttccaa catcggaagtaatactttagactggttccagcagctcccaggaacggcccccaaactcct catctttgatactaatcggcggccctcaggggtccctgaccgattctctggctccaagtc tggcacctcagcctccctggccatcagtggcctccaggctgaggatgaggctgtttactt ttgtgcaacatgggataacagcctcaacggcgcggtgttcggcggggtaccaagctcag cgtcccacgtcaggccaaggctgccccctcggtcactctgttcccgccctcctctgagga gcttcaagccaacaaggccacactggtgtgtctcataagtgacttctacccgggagccgt gacagtggcctggaaggcagatagcagccccgtcaaggcgggagtggagaccaccacacc ctccaaacaaagcaacaacaagtacgcggccagcagctatctgagcctgacgcctgagca gtggaagtcccacagaagctacagctgccaggtcacgcatgaagggagcaccgtggagaa gacagtggcccctacagaatgttcat

SEQ ID NO: 37

- m921 heavy chain nucleic acid sequence
caggtacagctgcagcagtcagg tccaggactggtgaagccctcgcagaccctctcactcacctgcgccatctccggggacag tgtctctagcaacagtgctgcctggaactggatcaggcagtccccatcgagaggccttga gtggctgggaaggacatactacaggtccaagtggtataatgactatgcagtatctgtgaa aggtcgaataaccatcaacccagacacatccaagaaccagttctccctgcagctgaactc tgtgactcccgaggacacggctgtgtattactgtgcaagagacttgggagtagcagcagc tgacagctactactactacggtatggacgtctggggccaagggaccacggtcaccgtctc ctcagcctccaccaagggcccatcggtcttccccctggcaccctcctccaagagcacctc tgggggcacagcggccctgggctgcctggtcaaggactacttccccgaaccggtgacggt gtcgtggaactcaggcgccctgaccagcggcgtgcacaccttcccggctgtcctacagtc ctcaggactctactccctcagcagcgtggtgaccgtgccctccagcagcttgggcaccca gacctacatctgcaacgtgaatcacaagcccagcaacaccaaggtggacaagaaagttgg gcccaaatcttgtgacaaaactagtggccaggccggc

SEQ ID NO: 38

- m922 light chain nucleic acid sequence
cagtctgtgctgactcagccaccctc agcgtctgggacccccgggcagagggtcaccatctcttgttctggaagcagctccaacat cggaagtaatactgtaaactggtaccagcagctcccaggaacggccccaaaactcctcat ctatagtaataatcagcggccctcaggggtccctgaccgattctctggctccaagtctgg cacctcagcctccctggccatcagtgggctccagtctgaggatgaggctgactattactg tgcagcatgggatgacagcctgaatggtcgcgtggcattcggcggagggaccaagctgac cgtcctaggccagcccaaggctgccccctcggtcactctgttcccaccctcctctgagga gcttcaagccaacaaggccacactggtgtgcctcataagcgacttctacccgggagccgt gacagtggcctggaaggcagaCagcagccccgtcaaggcgggagtggagaccaccacacc ctccaaacaaagcaacaacaagtacgcggccagcagctacctgagcctgacgcctgagca gtggaagtcccacaaaagctacagctgccaggtcacgcatgaagggagcaccgtggagaa gacagtggcccctacagaatgttca

SEQ ID NO: 39

- m922 heavy chain nucleic acid sequence
caggtacagctgcagcagtcag gtccaggaccggtgaagccctcgcagaccctctcactcacctgtgccatctccggggaca gtgtctctagcaacagtgctgcttggaactggatcaggcagtccccatcgagaggccttg agtggctgggaaggacacactacaggtccaagtggtataatgatcatgcagtatctgtga aaagtcgaataaccatcaacccagacacatccaagaaccagttctccctgcagctgaact ctgtgactcccgaggacacggctgtgtattactgtgcaagagaaacagtggctgttgatg cttttgatatctggggccaagggacaatggtcaccgtctcttcagcctccaccaagggcc catcggtcttccccctggcaccctcctccaagagcacctctgggggcacagcggccctgg gctgcctggtcaaggactacttccccgaaccggtgacggCgtcgtggaactcaggcgccc tgaccagcggcgtgcacaccttcccggctgtcctacagtcctcaggactctactccctca gcagcgtggtgaccgtgccctccagcagcttgggcacccagacctacatctgcagcgtga atcacaagcccagcaacaccaaggtggacaagaaagctgagcccaaatcttgtgacaaaa ctagtggccaggccggcca

What is claimed is:

1. An antibody that binds to and is an agonist of DR4, wherein the antibody comprises a heavy chain variable region and a light chain variable region, wherein the heavy chain variable region and the light chain variable region each comprise the following three complementary determining regions (CDRs): CDR1, CDR2 and CDR3; wherein:
   i) the CDR1 of the heavy chain variable region comprises the amino acid sequence of SEQ ID NO:8;
   ii) the CDR2 of the heavy chain variable region comprises the amino acid sequence of SEQ ID NO:9;
   iii) the CDR3 of the heavy chain variable region comprises the amino acid sequence of SEQ ID NO:10;
   iv) the CDR1 of the light chain variable region comprises the amino acid sequence of SEQ ID NO:5;
   v) the CDR2 of the light chain variable region comprises the amino acid sequence of SEQ ID NO:6;
   vi) the CDR3 of the light chain variable region comprises the amino acid sequence of SEQ ID NO:7.

2. The antibody of claim 1, wherein the antibody comprises the light chain variable segment (FR1-CDR1-FR2-CDR2-FR3) of SEQ ID NO:1 and the heavy chain variable segment (FR1-CDR1-FR2-CDR2-FR3) of SEQ ID NO:2.

3. The antibody of claim 1, wherein the antibody comprises a light chain variable region having at least 50% sequence identity to SEQ ID NO:1 and a heavy chain variable region having at least 50% sequence identity to SEQ ID NO:2.

4. The antibody of claim 3, wherein the antibody comprises a light chain variable region having at least 80% sequence identity to SEQ ID NO:1 and a heavy chain variable region having at least 80% sequence identity to SEQ ID NO:2.

5. The antibody of claim 1, wherein the antibody is a human antibody.

6. The antibody of claim 1, wherein the antibody is a multivalent antibody.

7. The antibody of claim 6, wherein the antibody is a multispecific antibody.

8. The antibody of claim 7, wherein the antibody is a bispecific antibody.

9. The antibody of claim 1, wherein the antibody is cross-linked.

10. A composition comprising an antibody of claim 1, and a pharmaceutically acceptable carrier.

11. A polynucleotide encoding an antibody of claim 1.

12. An expression cassette comprising the polynucleotide of claim 11.

13. A host cell comprising the expression cassette of claim 12.

14. A method of inducing apoptosis in a target cancer cell expressing DR4 comprising contacting the target cancer cell with an antibody of claim 1.

15. The method of claim 14, wherein the cell is in vivo.

16. The method of claim 14, wherein the cell is in vitro.

17. The method of claim 14, wherein the cell is a cancer cell.

18. A method of reducing or inhibiting the growth of a cancer expressing DR4 in a subject in need thereof, comprising administering to the subject a therapeutically effective amount of an antibody of claim 1.

19. The method of claim 18, further comprising administering to the subject an anticancer chemotherapeutic drug and/or irradiation.

20. A kit containing an antibody of claim 1 and a pharmaceutically acceptable carrier.

21. The kit of claim 20, further comprising a second agent for co-administration with the antibody.

* * * * *